United States Patent
Jeong

(10) Patent No.: US 10,500,411 B2
(45) Date of Patent: Dec. 10, 2019

(54) CANCER CELL GROWTH INHIBITION AND KILLING DEVICE USING BLUE LIGHT LED

(71) Applicant: INDUSTRIAL COOPERATION FOUNDATION CHONBUK NATIONAL UNIVERSITY, Jeollabuk-do (KR)

(72) Inventor: Hwan-Jeong Jeong, Jeollabuk-do (KR)

(73) Assignee: Industrial Cooperation Foundation Chonbuk National University, Jeonju-si (KR)

(*) Notice: Subject to any disclaimer, the term of this patent is extended or adjusted under 35 U.S.C. 154(b) by 0 days.

(21) Appl. No.: 15/324,036

(22) PCT Filed: Jul. 9, 2015

(86) PCT No.: PCT/KR2015/007116
§ 371 (c)(1),
(2) Date: Jan. 5, 2017

(87) PCT Pub. No.: WO2016/006942
PCT Pub. Date: Jan. 14, 2016

(65) Prior Publication Data
US 2017/0157419 A1    Jun. 8, 2017

(30) Foreign Application Priority Data

Jul. 9, 2014   (KR) .................. 10-2014-0086138
Jul. 9, 2015   (KR) .................. 10-2015-0097581

(51) Int. Cl.
*A61N 5/06* (2006.01)
(52) U.S. Cl.
CPC .......... *A61N 5/0613* (2013.01); *A61N 5/0616* (2013.01); *A61N 2005/064* (2013.01);
(Continued)

(58) Field of Classification Search
CPC ............... A61N 5/0613; A61N 5/0616; A61N 2005/0638; A61N 2005/064;
(Continued)

(56) References Cited

U.S. PATENT DOCUMENTS 5,891,186 A * 4/1999 Daffer .................... A61H 23/02
                                                          600/21
2003/0187487 A1* 10/2003 Griffith ................ A61N 5/0614
                                                          607/94
(Continued)

FOREIGN PATENT DOCUMENTS

JP        2005065977 A      3/2005
KR    20020093686 A    12/2002
(Continued)

*Primary Examiner* — Aaron F Roane
(74) *Attorney, Agent, or Firm* — Norton Rose Fulbright US LLP

(57) ABSTRACT

Provided is a cancer cell growth inhibition and killing device using a blue light LED. The present invention comprises: a bed part which has a top plate on which the body is laid to stand by; a main body part provided with a treatment space, which has a predetermined size and on which the bed part is disposed, and having a chamber which is divided by the treatment space and a transparent plate formed of a light-transmitting material to thus form a treatment light generation space; and a treatment light generation unit which generates a treatment light having a wavelength band of a predetermined size when power is applied so that the treatment light can penetrate the subcutaneous tissue of the body and thereby stimulate and kill cancer cells moving along blood vessels, and which is provided in the chamber so as to irradiate the treatment space with the treatment light after the treatment light has penetrated though the transparent plate.

6 Claims, 23 Drawing Sheets

(52) U.S. Cl.
CPC .............. *A61N 2005/0638* (2013.01); *A61N 2005/0652* (2013.01); *A61N 2005/0663* (2013.01); *A61N 2005/0666* (2013.01)

(58) Field of Classification Search
CPC .... A61N 2005/0652; A61N 2005/0663; A61N 2005/0666
USPC .......................................................... 607/91
See application file for complete search history.

(56) References Cited

U.S. PATENT DOCUMENTS

| | | | | |
|---|---|---|---|---|
| 2007/0088410 | A1* | 4/2007 | Chung | A61N 5/0621 607/91 |
| 2007/0208395 | A1* | 9/2007 | Leclerc | A61N 5/0616 607/86 |
| 2009/0005839 | A1* | 1/2009 | Griffith | A61N 5/0614 607/91 |
| 2014/0288351 | A1* | 9/2014 | Jones | A61N 5/06 600/9 |

FOREIGN PATENT DOCUMENTS

| | | |
|---|---|---|
| KR | 20090120351 A | 11/2009 |
| KR | 20140025154 A | 3/2014 |
| KR | 20140050497 A | 4/2014 |

* cited by examiner

CANCER CELL GROWTH INHIBITION AND KILLING DEVICE USING BLUE LIGHT LED

CROSS-REFERENCE TO RELATED APPLICATIONS

This application is a national phase application under 35 U.S.C. § 371 of International Application No. PCT/KR2015/007116 filed Jul. 9, 2015, which claims priority to Republic of Korea Patent Application No. 10-2014-0086138 filed Jul. 9, 2014, and Republic of Korea Patent Application No. 10-2015-0097581 filed Jul. 9, 2015. The entire contents of each of the above-referenced disclosures are specifically incorporated herein by reference without disclaimer.

TECHNICAL FIELD

The present invention relates to a device capable of inhibiting growth of cancer cells and killing and treating the cancer cells by using an LED generating blue light, and more particularly, to a cancer cell growth and killing device using a blue light LED capable of inhibiting growth or killing the cancer cells which move along the blood vessels in addition to skin cancer cells, leukemia, skin cancer such as lymphoma, and blood cancer by irradiating blue light generated from an LED to a subcutaneous tissue when power is applied.

BACKGROUND ART

Even today, with rapid development of medical technology, cancer is a disease that has not yet been completely overcome, and still, many people are diagnosed with cancer and killed in cancer or its associated complications.

Accordingly, with respect to a method and a device for pre-diagnosing and preventing the cancer and treating the cancer, a lot of studies have been conducted for a long time, and as such, with development of biotechnology related to the cancer, various devices and methods for cancer treatment have been used from the related art.

A therapy using light among various cancer cell therapy devices is a therapeutic method which is classified into new fields of a photodynamic therapy (PDT) and a photothermal therapy (PTT) to be developed.

The PDT is a therapeutic method of treating directly and indirectly a lesion site by a photosensitive agent activated by light by irradiating light after coating or injecting the photosensitive agent.

A principle of using the PDT to cancer treatment is to administrate the photosensitive agent sensitive to light instead of a direct optical component to a patient, selectively accumulate the photosensitive agent only in cancer tissue cells after a predetermined time, and specifically remove only the cancer tissue without response in a normal tissue when a predetermined-wavelength laser suitable for the photosensitive agent is irradiated to the diseased part.

However, for scientific reasons that it is actually very difficult to selectively accumulate the photosensitive agent in the cancer tissue cells, today, treatment of various cancer cells utilizing the PDT has been researched, but is not actually utilized.

Further, the PDT has been clinically used in fields of treatment of dermatological diseases, infections and injuries other than the treatment field of cancer.

In terms of the device, a photodynamic therapeutic device is constituted by a light source generation device that activates a photosensitive agent by generating light having a predetermined wavelength such as a laser, a light transfer device such as a light fiber cable that transfers light to the diseased part from the light source generation device, and a light irradiation device that irradiates the light transferred through the light transfer device to the diseased part.

In researches to treat superficial tumors such as skin cancer by a photodynamic therapeutic method, it can be seen that there is an effect in cell experiments or some animal experiments in some researches, but as a therapeutic method that is not actually used, the reason is that a first treatment principle of the superficial tumors is surgery and the superficial tumors can be primarily removed by the surgery.

Further, the reason why there is no example of treating a tumor in a deep part by a photodynamic therapeutic method until now is that it is very difficult to determine sites of tumors and the number of tumors in order to exactly irradiate the tumors and problems of accumulation and toxicity of the photosensitive agent for cancer cells, methodological difficulties of light irradiation, and the like are scattered.

The treatment by the PTT does not also show a direct treatment effect by light by injecting and then implementing a medium, that is, gold nanoparticles that causes resonance by receiving light to convert the resonance into heat energy.

Besides, treatment using plasma is performed in a research level, but there is no example proven through animal experiments until now, and the possibility is very slightly shown by results of proving any effect through cell experiments and the result of the cell experiments does not prove the result of animal experiments.

The reason is that the use in the cell experiment is not the assumption of the actual situation, but there is only a result in the cells. For example, even though skin cancer cells or rectal cancer cells are incubated in a flask in a laboratory and damaged by irradiating light to the flask, it is not shown that the skin cancer or the rectal cancer is treated by the light, but it is shown that the skin cancer cells or the rectal cancer cells are damaged at a laboratory level.

Actually, in order to show the treatment effect of the skin cancer or the rectal cancer, the skin cancer cells or the rectal cancer cells are transplanted in the animal and more exactly, not heteroplastically transplanted but orthotopically transplanted, and as a result, the possibility needs to be evaluated.

As described above, the PTT and the PDT that indirectly use the light in the treatment using the light have been researched, but it is clear that the treatment is not performed by the light but a photosensitive agent or a material capable of generating heat and there is no example that shows the exact treatment effect in cancer cells by directly using the light.

The plasma also shows some examples at an experimental cell research level and does not provide a result capable of treating the cancer cells as a result in the living body.

(Patent Document 1) KR2011-0131453 A

DISCLOSURE

Technical Problem

Therefore, an object of the present invention is to provide a cancer cell growth inhibition and killing device using a blue light LED capable of inhibiting growth or killing the cancer cells which move along the blood vessels in addition to skin cancer cells, leukemia, skin cancer such as lymphoma, and blood cancer by irradiating blue light generated from an LED to a subcutaneous tissue when power is applied.

Other technical objects desired to be achieved in the present invention are not limited to the aforementioned objects, and other technical objects not described above will be apparent to those skilled in the art from the disclosure of the present invention.

Technical Solution

An aspect of the present invention provides a cancer cell growth inhibition and killing device using a blue light LED, including: a bed part which has a top plate on which the body is laid to stand by; a main body part provided with a treatment space, which has a predetermined size and on which the bed part is disposed, and having a chamber which is divided by the treatment space and a transparent plate formed of a light-transmitting material to thus form a treatment light generation space; and a treatment light generation unit which generates a treatment light having a wavelength band of a predetermined size when power is applied so that the treatment light can penetrate the subcutaneous tissue of the body and thereby stimulate and kill cancer cells moving along blood vessels, and which is provided in the chamber so as to irradiate the treatment space with the treatment light after the treatment light has penetrated though the transparent plate.

Preferably, the treatment light generation unit may include LEDs that generate blue treatment light having a wavelength band of 450 to 470 nm when the power is applied, lenses that guide light so that the blue treatment light generated in the LED is convergence-irradiated to the body, and heat dissipation members that discharge heat generated when the light of the LED is emitted to the outside so that a central wavelength of the blue treatment light is not changed.

Preferably, the main body part may include at least one ventilation fan at the outside of the chamber corresponding to the treatment light generation space to ventilate indoor air in the treatment light generation space to the outside.

Preferably, the main body part may include a reflective sheet that reflects the treatment light to the inner surface to enhance a light irradiation rate for the living body.

Preferably, the main body part may include an upper main body part having the upper treatment light generation space based on the bed part, a lower main body part having the lower treatment light generation space, and a hinge member pivoting the upper main body part with respect to the lower main body part to open and close the treatment space.

Preferably, the bed part may include a vertical table having a predetermined length of which an upper end is rotatably supported through a hinge pin on the lower surface of the top plate and front and rear cylinder members of which load front ends are connected to front and rear lower surfaces of the top plate through the pin member and are vertically operated to obliquely shift a horizontal state of the top plate based on the hinge pin, respectively.

More preferably, the vertical table may include an internal pipe having a predetermined length of which an upper end is connected to the top plate through the hinge pin and an external pipe having a predetermined length to which a lower end of the internal pipe is inserted to be vertically guided.

Advantageous Effects

According to preferred exemplary embodiments of the present invention, there are the following effects.

(1) Blue treatment light having high transmittance and a short wavelength band is irradiated to the living body to efficiently inhibit growth of cancer cells moving along the blood vessels by the treatment light transmitted through the subcutaneous tissue and enhance the cure rate by apoptosis.

(2) The overall configuration is simplified to reduce manufacturing costs and a treatment process is not complicated but simplified to enhance ease of use of the device.

(3) The inclination of the top plate on which the body is laid is adjusted to accelerate heart beat and blood circulation in the blood vessel system, thereby enhancing treatment efficiency by irradiating blue treatment light for the cells moving along the blood vessels.

DESCRIPTION OF DRAWINGS

FIG. 9A to 9C are a graph illustrating cell viability in Experimental Example 5, in which FIG. 9A is an analysis result of viability in a A20 cell line, FIG. 9B is an analysis result of viability in a RAMOS cell line, and FIG. 9C is an analysis result of viability in a normal lymphocyte in Comparative Example 1.

FIGS. 10A and 10B are a flow cytometry result of Experimental Example 6, in which FIG. 10A is a flow cytometry result of viability in a A20 cell line, and FIG. 10B is a flow cytometry result in a RAMOS cell line.

FIGS. 18A and 18B are a photograph of an animal experimental result for a blue treatment light-irradiated group and a non-irradiated control group, in which FIG. 18A is a control group, and FIG. 18B is an irradiated group.

BEST MODE

Figure 1A:
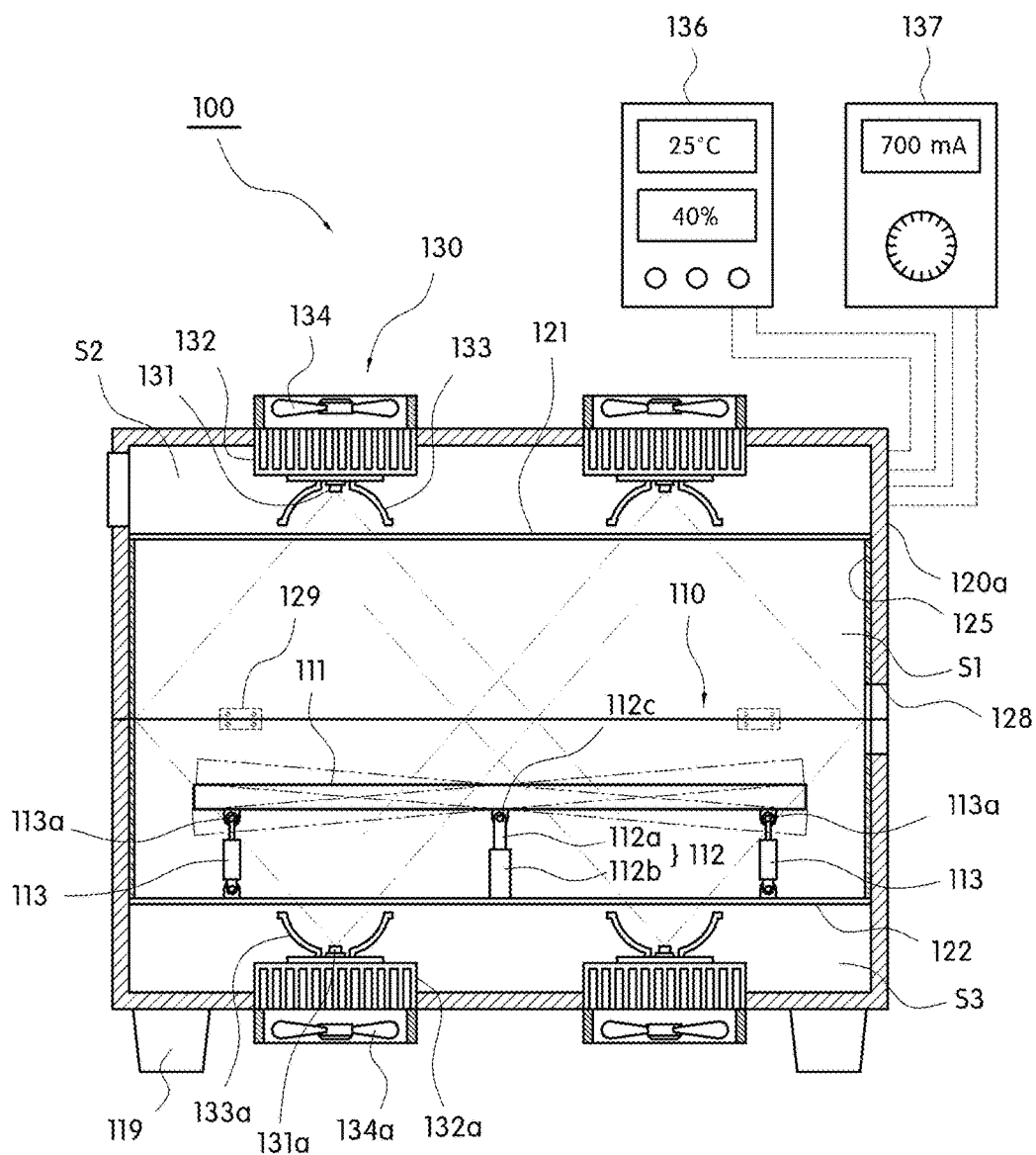
FIG. 1A is a cross-sectional view when a cell cancer growth inhibiting and killing device using a blue light LED according to a preferred embodiment of the present invention is viewed from the front.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 1B:
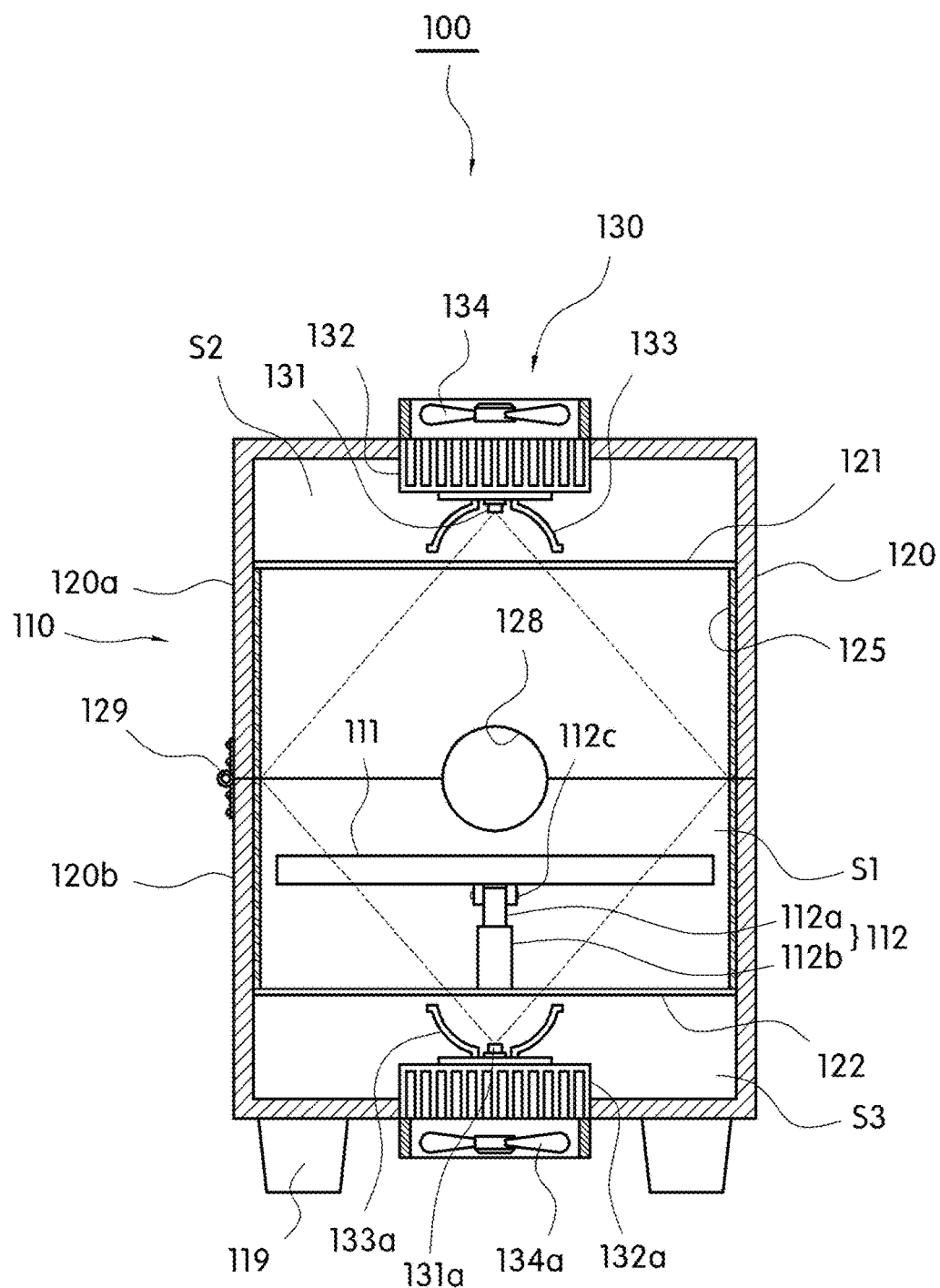
FIG. 1B is a cross-sectional view when the cell cancer growth inhibiting and killing device using a blue light LED according to the preferred embodiment of the present invention is viewed from the side.

A cancer cell growth inhibition and killing device 100 using a blue light LED according to a preferred embodiment of the present invention includes a bed part 110, a main body part 120, and a treatment light generation unit 130, as illustrated in FIGS. 1A and 1B.

The bed part 110 includes a top plate 111 on which a body of a patient with cancer cells such as skin cancer is laid to stand by, and the top plate 111 may be formed of a substantially square-shaped transparent plate to transmit the blue treatment light provided from the treatment light generation unit 130 while the patient to treat the cancer cell is laid to stand by.

The main body part 120 is a structure including a treatment space 51, on which the bed part is disposed and which has a predetermined size of internal volume to perform substantial cancer cell treatment by blue light as the treatment light and a support 119 spaced apart from the ground.

The main body part 120 includes a chamber forming treatment light generation spaces S2 and S3 which are vertically divided by the treatment space S1 on which the bed part 110 is disposed and transparent plates 121 and 122 formed of a light-transmitting material.

It is illustrated that the treatment light generation spaces S2 and S3 are at the top and the bottom of the treatment space S1, respectively, but the treatment light generation spaces S2 and S3 are not limited thereto and may be included only at the top of the treatment space S1.

Herein, the main body part 120 includes an upper main body part 120a having the upper treatment light generation space S2 based on the bed part 110, a lower main body part 120b having the lower treatment light generation space S3, and a hinge member 129 pivoting the upper main body part 120a with respect to the lower main body part 120b to open and close the treatment space S1.

Accordingly, the main body part 110 vertically divided into the upper and lower main body parts 120a and 120b pivots up the upper main body part based on a hinge pin of the hinge member 120 to expose the bed part 110 to the outside and pivots down and covers the upper main body part while the patient is laid on the bed part.

The treatment light generation unit 130 is included in a chamber which has a light source generating treatment light having a predetermined size of wavelength band when power is applied to form the treatment light generation space to penetrate and irradiate the treatment light generated from the light source to the treatment space S1 through the transparent plates 121 and 122.

The treatment light generation unit 130 includes LEDs 131 and 131a that generate the blue treatment light having a wavelength band of 450 to 470 nm when the power is applied, lenses 132 and 132a that guide lights so that the blue treatment light generated from the LED is not diffused, but convergence-irradiated to the body, and heat dissipation members 133 and 133a that discharge heat generated when the light of the LED is emitted to the outside so that a central wavelength of the blue treatment light is not changed.

Further, preferably the main body part 120 may include at least one ventilation fan 134 at the outside of the chamber corresponding to the treatment light generation space to ventilate indoor air in the treatment light generation space which is converted into a hot air atmosphere by heat generated when the light of the LED is emitted.

Herein, preferably, the light source may be electrically connected with a variable power supply part 137 that varies intensity of current applied to the LED to vary a wavelength band of the blue treatment light and include a temperature and humidity measurement unit 136 that measures internal temperature and internal humidity of the treatment space S1 and the treatment light generation spaces S2 and S3 and displays the measured temperature and humidity values.

In addition, the main body part 120 may be made of an opaque material so as not to transmit the blue treatment light generated from the light source to the outside.

In addition, the main body part 120 which forms the treatment space treating the cancer cells by irradiating the blue treatment light generated from the light source to the patient which is laid to stand by on the bed part may be formed in a substantially rectangular or cylindrical shape, and the treatment space may be vertically divided or integrated.

Figure 2A:
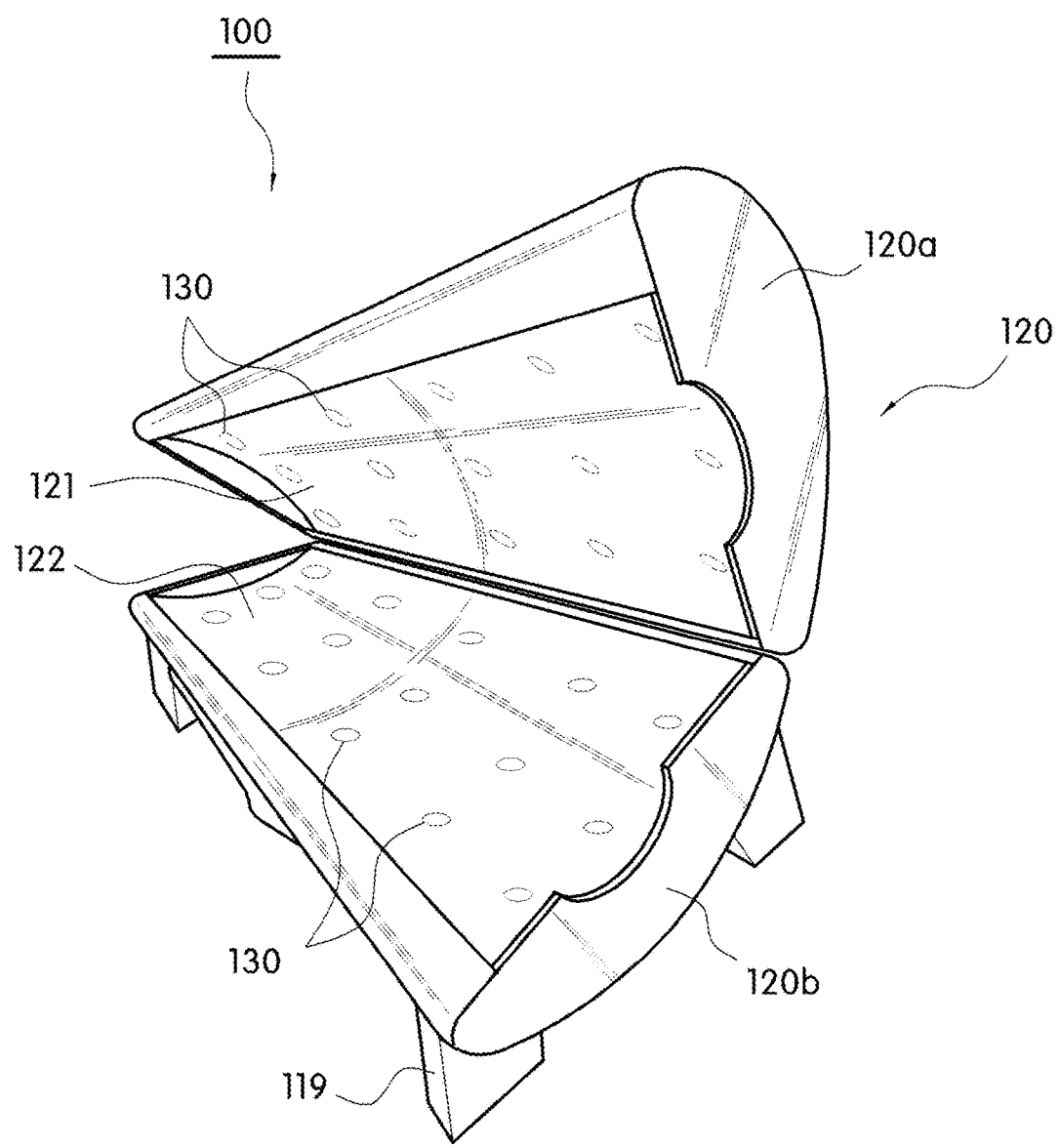
FIG. 2A is a perspective view of the cell cancer growth inhibiting and killing device using a blue light LED according to the preferred embodiment of the present invention which is implemented in a cylindrical shape.

Further, as illustrated in FIG. 2A, the main body part 120 is vertically divided into the upper and lower main body parts 120a and 120b to be pivoted through the hinge member and formed in a cylindrical shape having a hollow part in which most of the body of the patient except for the head is disposed during assembly, and the top plate of the bed part on which the patient is laid is replaced with the upper transparent plate 122 forming the lower treatment light generation space to remove the configuration of the bed part, thereby simplifying the overall configuration.

Figure 2B:
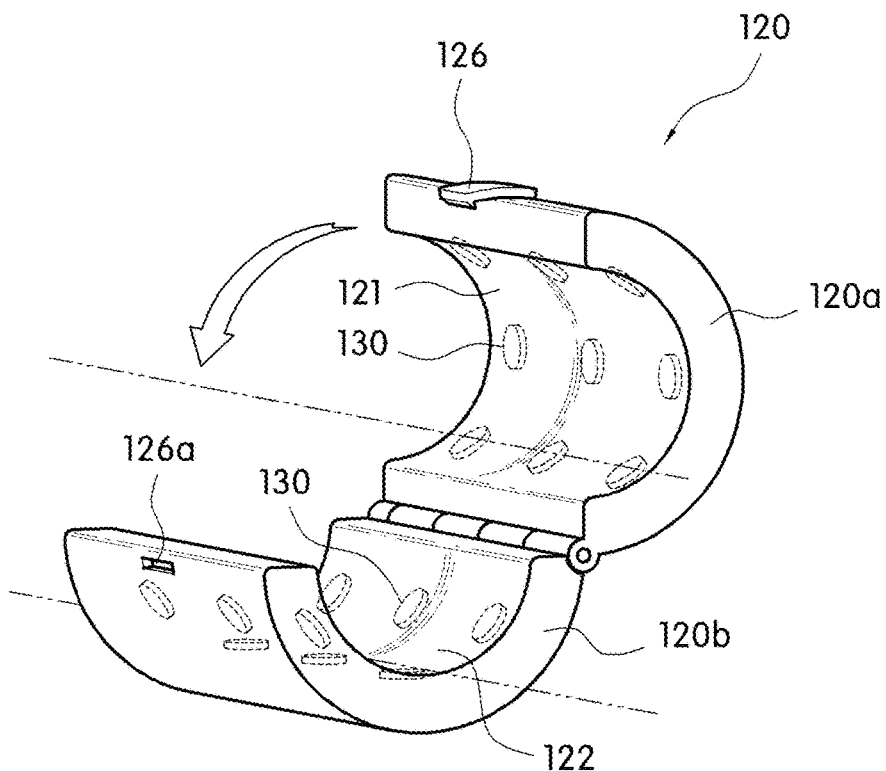
FIG. 2B is a perspective view of the cell cancer growth inhibiting and killing device using a blue light LED according to the preferred embodiment of the present invention which is implemented in a handy type for local treatment.

In addition, as illustrated in FIG. 2B, the main body part 120 is vertically divided into the upper and lower main body parts 120a and 120b so that the treatment of the local portion of the patient's body such as arms and legs is possible and handling is possible to be pivoted through the hinge member and formed in a cylindrical shape having a hollow part in which arms or legs which is the local portion of the patient's body is disposed during assembly, and the upper and lower transparent plates 121 and 122 contacting the arms or the legs may be formed in an arc cross-sectional shape.

The upper and lower main body parts 120a and 120b may include a holder 126 to stably maintain a combined cylindrical shape and a connection groove 126a to elastically engage the end of the holder.

On the inner surface of the main body part 120 forming the treatment space S1 to which the blue treatment light is transmitted and irradiated, a reflective sheet 125 may be included to enhance a light irradiation rate for the skin of the patient by increasing reflective efficiency of the blue treatment light.

Accordingly, when the blue treatment light having the shortest wavelength band of 450 to 470 nm in a visible light band is irradiated to the body of the patient which is laid on the top plate 111 or the lower transparent plate of the bed part 110, transmittance through the subcutaneous tissue is increased by energy increased as the wavelength is decreased, and thus the blue treatment light passing through the subcutaneous tissue stimulates the cancer cells moving along the blood vessels to inhibit the growth and induce apoptosis.

The apoptosis is to treat cancer cells when the cancer cells irradiated by the blue treatment light are treated as abnormal cells, damaged cells, or aged cells and killed.

Meanwhile, the bed part 110 includes a vertical table 112 of which an upper end is rotatably supported through a hinge pin 112c on the lower surface of the top plate 111 and front and rear cylinder members 113 of which load front ends are connected to front and rear lower surfaces of the top plate 111 through the pin member 113a and are vertically operated to obliquely shift a horizontal state of the top plate based on the hinge pin, respectively.

Further, the vertical table 112 includes an internal pipe 112a having a predetermined length of which an upper end is connected to the top plate through the hinge pin 112c and an external pipe 112b having a predetermined length to which a lower end of the internal pipe is inserted to be vertically guided.

Accordingly, when the top plate 111 is shifted from the horizontal state to an inclined state which is inclined at a predetermined angle at any one side of the front end or the rear end by upper and lower portions of any one cylinder member of the front and rear cylinder members 113, while the heart rate of the patient which is laid on the top plate is increased, the circulation rate of the blood is increased, thereby enhancing an effect of treating the cancer cells by the blue treatment light.

When the front and rear cylinder members 113 ascend and descend, the top plate 111 may be approached to or separated from the treatment light generation space S2 formed in the upper chamber by appropriately adjusting a vertical height by an assembly structure of the vertical table 112 so that the internal pipe are vertically movable in the external pipe.

Meanwhile, the main body part 120 may include an opening 128 having a predetermined size so that the head of the patient laid on the bed part is exposed to the outside to prevent optic nerve damage or eye damage by irradiating the blue treatment light having energy to the face of the patient while the cancer cells moving along the blood vessels of the subcutaneous tissue are treated by irradiating the blue treatment light to the skin of the patient laid on the bed part 110.

EXAMPLES

Preparation Example 1. Preparation of Culture Cells

Preparation Example 1-1. Melanoma Cell Line B16F10

B16-F10 cells (American Type Culture Collection (ATCC), CRL-6475) were incubated at 37° C. by using a RPMI 1640 medium containing 10% fetal bovine serum, 0.25 µg/ml of amphotericin B and 10 µg/ml of gentamicin.

Preparation Example 1-2. Leukemia Cancer Cells A20

An A20 cell line (American Type Culture Collection (ATCC), TIB-208) was incubated at 37° C. by using a RPMI1640 medium containing 10% fetal bovine serum, 0.25 µg/ml of amphotericin B, 10 µg/ml of gentamicin and 0.05 mM 2-mercaptoethanol.

Preparation Example 1-3. Lymphoma Cell Line RAMOS

A RAMOS cell line (American Type Culture Collection (ATCC), CRL-1596) was incubated at 37° C. by using an IMDM medium containing 10% fetal bovine serum, 0.25 µg/ml of amphotericin B and 10 µg/ml of gentamicin.

Preparation Example 1-4. Human Fibrosarcoma Cell Line HT-1080

A HT-1080 cell line (American Type Culture Collection (ATCC), CCL-121) was incubated at 37° C. by using a DMDM medium containing 10% fetal bovine serum, 0.25 µg/ml of amphotericin B and 10 µg/ml of gentamicin.

Comparative Example 1. Lymphocytes of Normal Human Blood

In order to isolate lymphocytes from the normal blood, the normal blood was collected and immediately mixed with heparin to prevent blood clotting and then carefully placed on an equivalent amount of lymphocyte separation medium (Intron biotechnology, 21186) so as not to be mixed. The normal blood was centrifuged at room temperature for 15 mins at a speed of 400×g and then only the lymphocytes of a middle layer were collected in a new tube. The lymphocytes were washed twice with a RPMI 1640 medium without the same amount of fetal bovine serum as the lymphocytes and then suspended in the RPMI 1640 medium with 10% fetal bone serum and the normal lymphocytes were prepared.

Experimental Example 1. Measurement of Viability of Melanoma Cells

Figure 3:
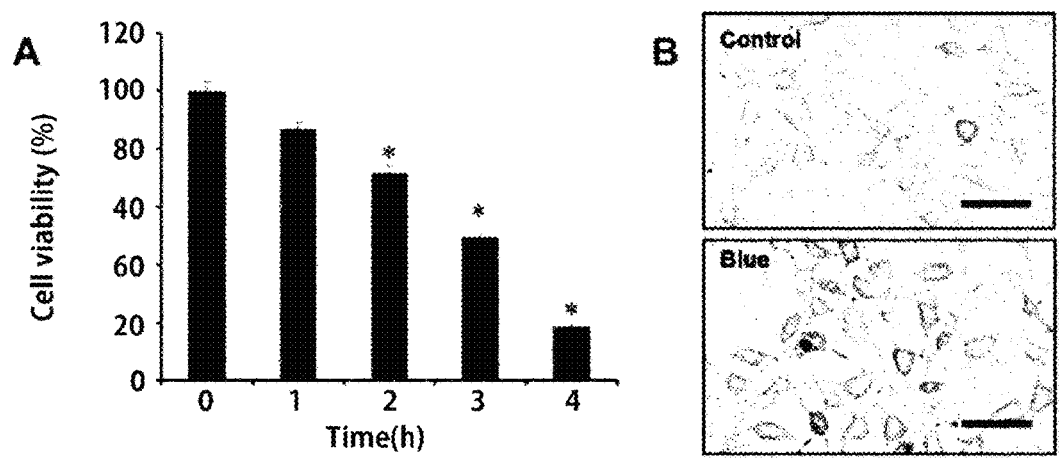
FIG. 3 is an analysis result of viability in melanoma cells in Experimental Example 1.

Melanoma cells incubated in Preparation Example 1-1 were divided to $5 \times 10^4$/well in a 4-well plate, irradiated with an LED of 450 nm for 1 hr to 4 hrs at 15.6 mW/cm$^2$, added with 10 µl of an MTT reagent at a concentration of 5 mg/ml, incubated at 37° C. for 4 hrs, and then cell viability was measured by measuring absorbance at 450 nm by using an ELISA reader and a measurement result was illustrated in FIG. 3.

As verified in FIG. 3, it was verified that when the LED blue treatment light was irradiated for 4 hrs, viability of B16-F10 cells was suppressed up to about 80% with a morphological change of cells.

Experimental Example 2. Flow Cytometry of Melanoma Cells

Melanoma cells incubated in Preparation Example 1-1 were divided by $1 \times 10^6$/dish in a dish of 6 cm, irradiated with LED blue treatment light of 450 nm for 1 hr to 4 hrs at 15.6 mW/cm², and then washed twice with a phosphate buffered saline (PBS). Thereafter, the melanoma cells were analyzed by using a kit (Biolegend, 640914) of detecting apoptosis by staining the cells with Annexin V with FITC and propidium iodide (PI). After staining the cells by adding 2.5 µl of Annexin V and 5 µl of propidium iodide (PI), early apoptosis, late apoptosis, and a percentage of dead cells were analyzed by using a flow cytometer (BD biosciences, FACSCalibur) and the analyzed result was illustrated in FIG. 4.

Figure 4:
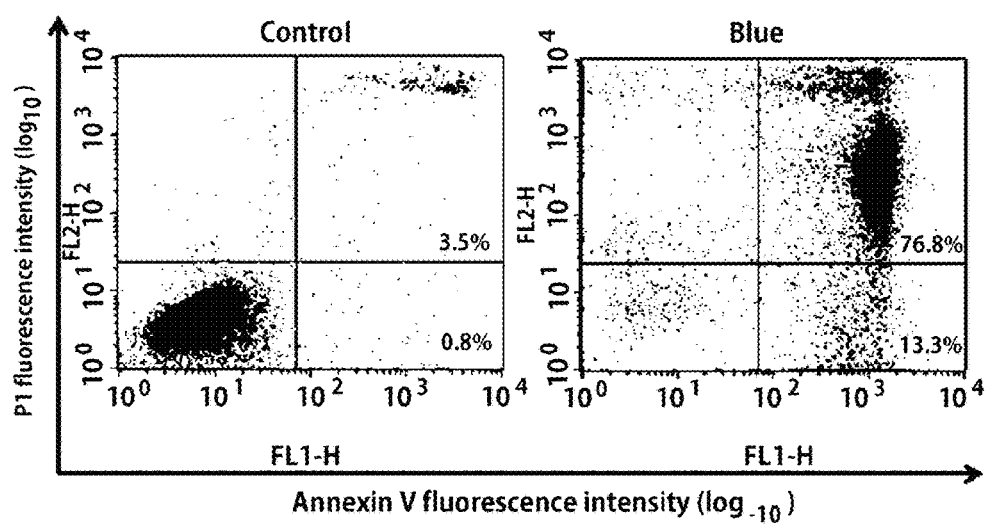
FIG. 4 is an analysis result of early apoptosis, late apoptosis, and a dead cell ratio in Experimental Example 2.

As verified in FIG. 4, the death of the cells verified in FIG. 3 were analyzed by using a flow cytometer after staining the cells by Annexin V and PI as markers of apoptosis, and as a result, the early apoptotic cells and the late apoptotic cells were 13.3% and 76.8%, respectively.

Figure 5:
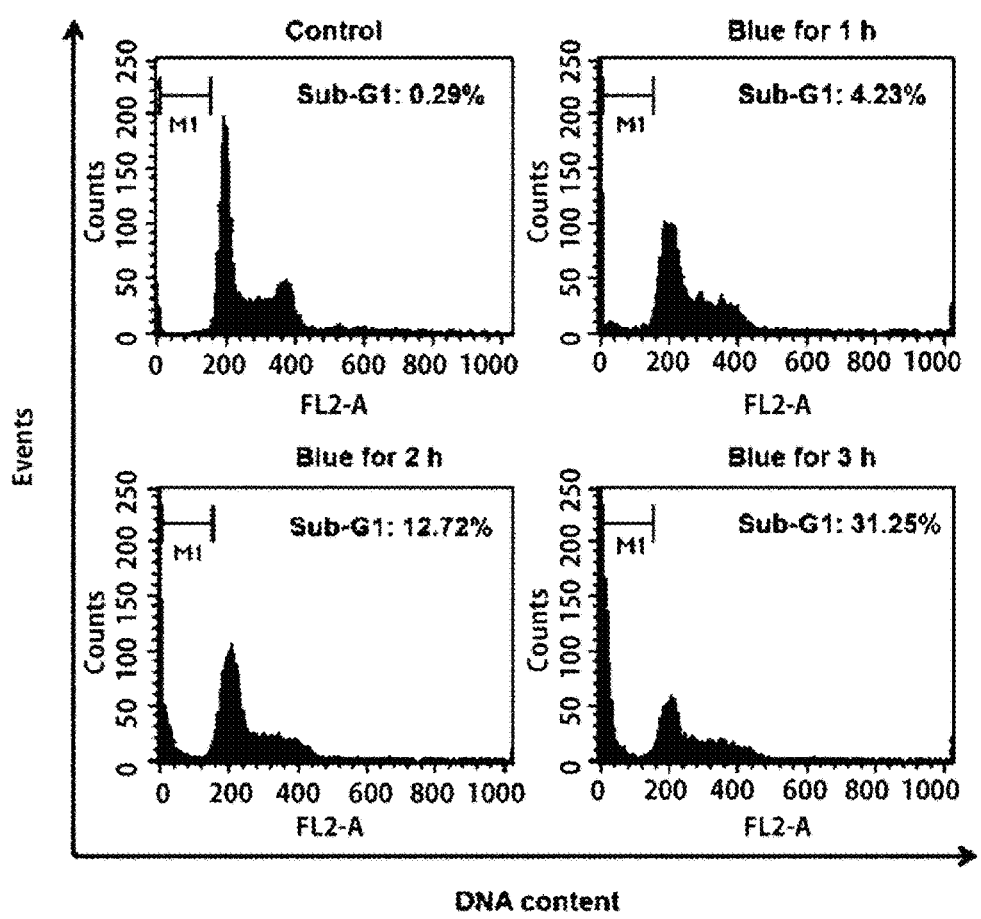
FIG. 5 is an observation result in Experimental Example 2.

Thereafter, sub-G1 arrest of the PI-stained cells was observed by using a flow cytometer (BD biosciences, FACSCalibur) and the observed result is illustrated in FIG. 5.

As verified in FIG. 5, in a change of cell cycle after irradiating the LED blue treatment light, it can be seen that cell accumulation to the sub-G1 group as the marker of the apoptosis is increased to 12.7% and 31.2% at 2 hrs and 3 hrs after irradiating the LED blue treatment light, respectively.

The result is that viability of cells in addition to biochemical and morphological changes is reduced through the apoptosis process of the melanoma cells by irradiating the LED blue treatment light.

Experimental Example 3. Measurement of Change in Mitochondria after LED Irradiation of Melanoma Cells Melanoma cells incubated in Preparation Example 1-1 were divided by 1×10⁶/dish in a dish of 6 cm, irradiated with LED blue treatment light of 450 nm for 1 hr to 4 hrs at 15.6 mW/cm², and then washed twice with a phosphate buffered saline (PBS). Thereafter, the melanoma cells were stained by adding 0.1 µg/ml of rhodamine 123 and then the membrane permeability of mitochondria was analyzed by using a flow cytometer and the analysis result was illustrated in FIG. 6.

Figure 6:
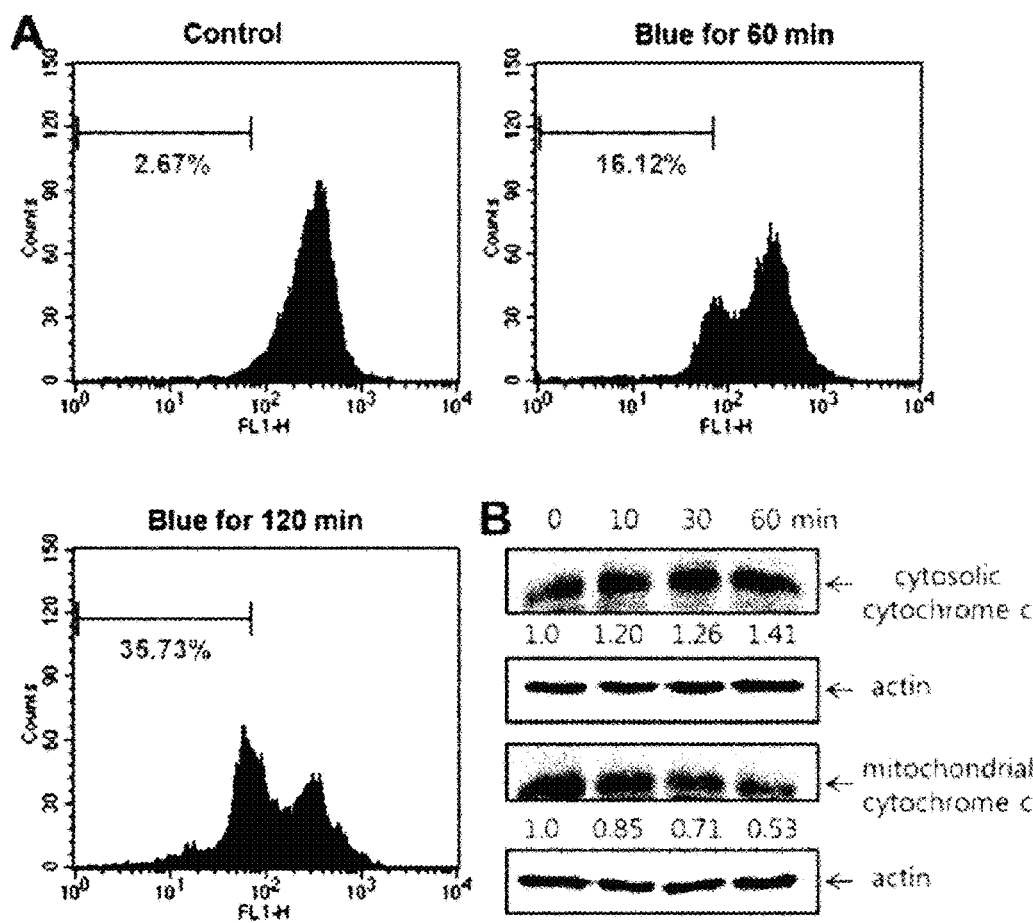
FIG. 6 is an analysis result of cell membrane permeability of mitochondria in Experimental Example 3.

As verified in FIG. 6, since loss of a potential difference in an inner membrane of mitochondria is a characterized in early stage of apoptosis, the potential difference in the inner membrane is reduced and thus while the outer membrane of the mitochondria burst, pro-apoptotic proteins containing cytochrome c are released into the cytoplasm. It was verified that after irradiation of the blue treatment light, the permeability of the inner membrane of the mitochondria was increased over time and expression of the cytochrome c protein in the cytoplasm was increased 1.2 times and 1.4 times for 30 mins to 60 mins after LED irradiation compared to a control group, respectively.

Further, the melanoma cells washed with the PBS was added with a cell destruction and protein extraction solution to extract the proteins from the cells and then the cell debris and the proteins were separated through centrifugation. The extracted proteins were moved to a membrane by electric force using a kit after electrophoresis and then reacted with antibodies of cytochrome c, phospho-p53, caspase-3, and poly ADP ribose polymerase (PARP), and reacted with secondary antibodies labeled with a luminescent material. Herein, the extracted proteins were reacted with an ECL reagent (Millipore, WBKLS0100) reacting with the luminescent material and thus the expression level of the proteins was measured by measuring the luminescence by using Fusion FX7 (Vilber lourmat). The measurement result is illustrated in FIG. 7.

Figure 7:
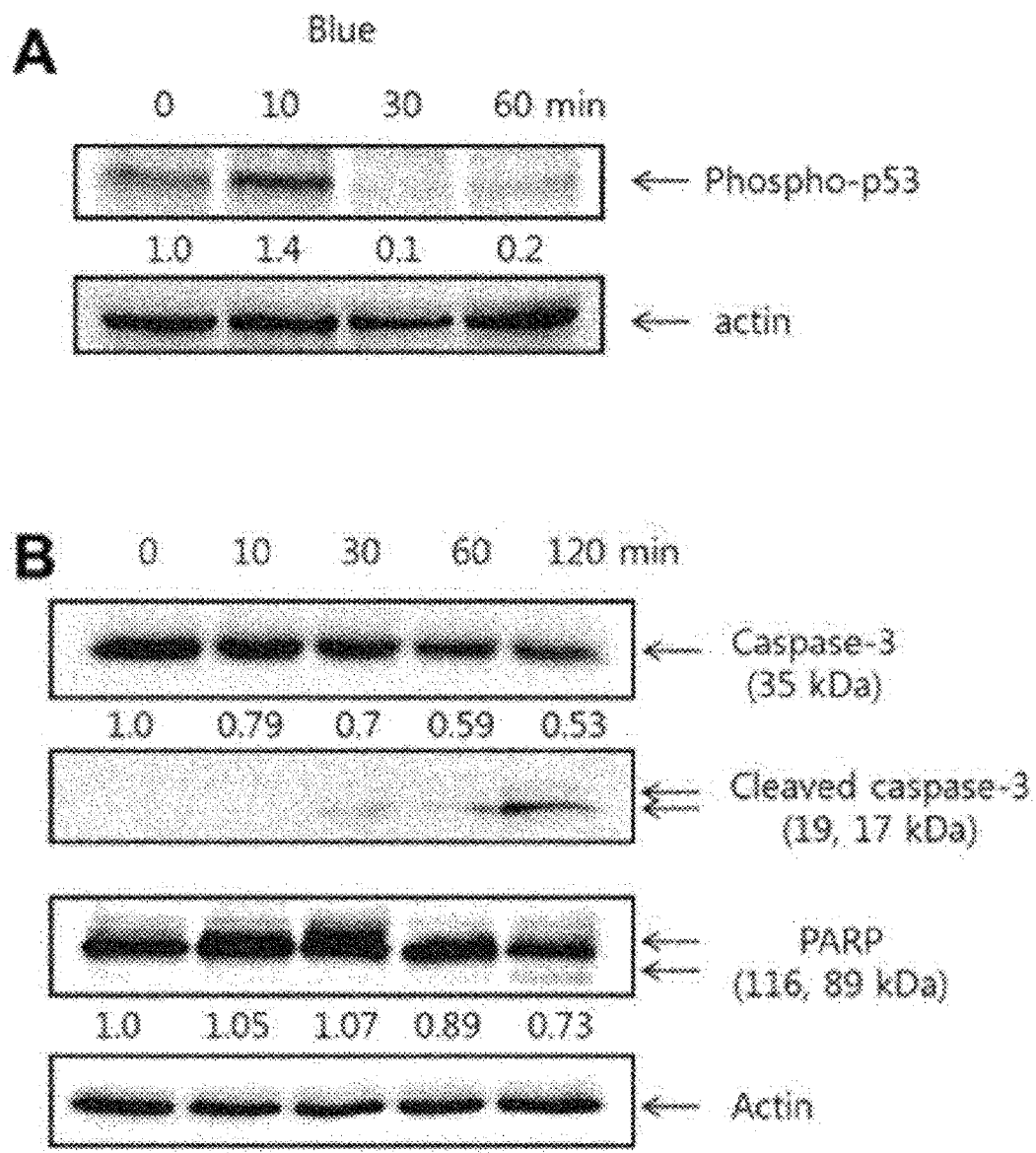
FIG. 7 is a result of measuring expression levels in Experimental Example 3.

As verified in FIG. 7, it can be verified that phosphorylation of p53 and cleavage of caspase-3 and PARP are increased after irradiating the LED blue treatment light. The result is that it is determined that after irradiating the LED blue treatment light, the DNA damage is generated and cell cycle arrest in addition to phosphorylation of p53, release of cytochrome c due to reduction of the membrane potential of mitochondria, and apoptosis through an apoptotic pathway by caspase occur.

Experimental Example 4. Melanoma Mouse Experiment

B16-F10 cells (American Type Culture Collection (ATCC), CRL-6475) were injected to the right sole of a C57BL/6 mouse, irradiated with LED blue treatment light of 450 nm at 15.6 mW/cm² for 3 hrs, paused for 5 hrs, and then repeated 39 times for 13 days, and the size of the tumor and metastasis of B16-F10 cells in the lymph node were observed. The measurement result is illustrated in FIG. 8.

Figure 8:
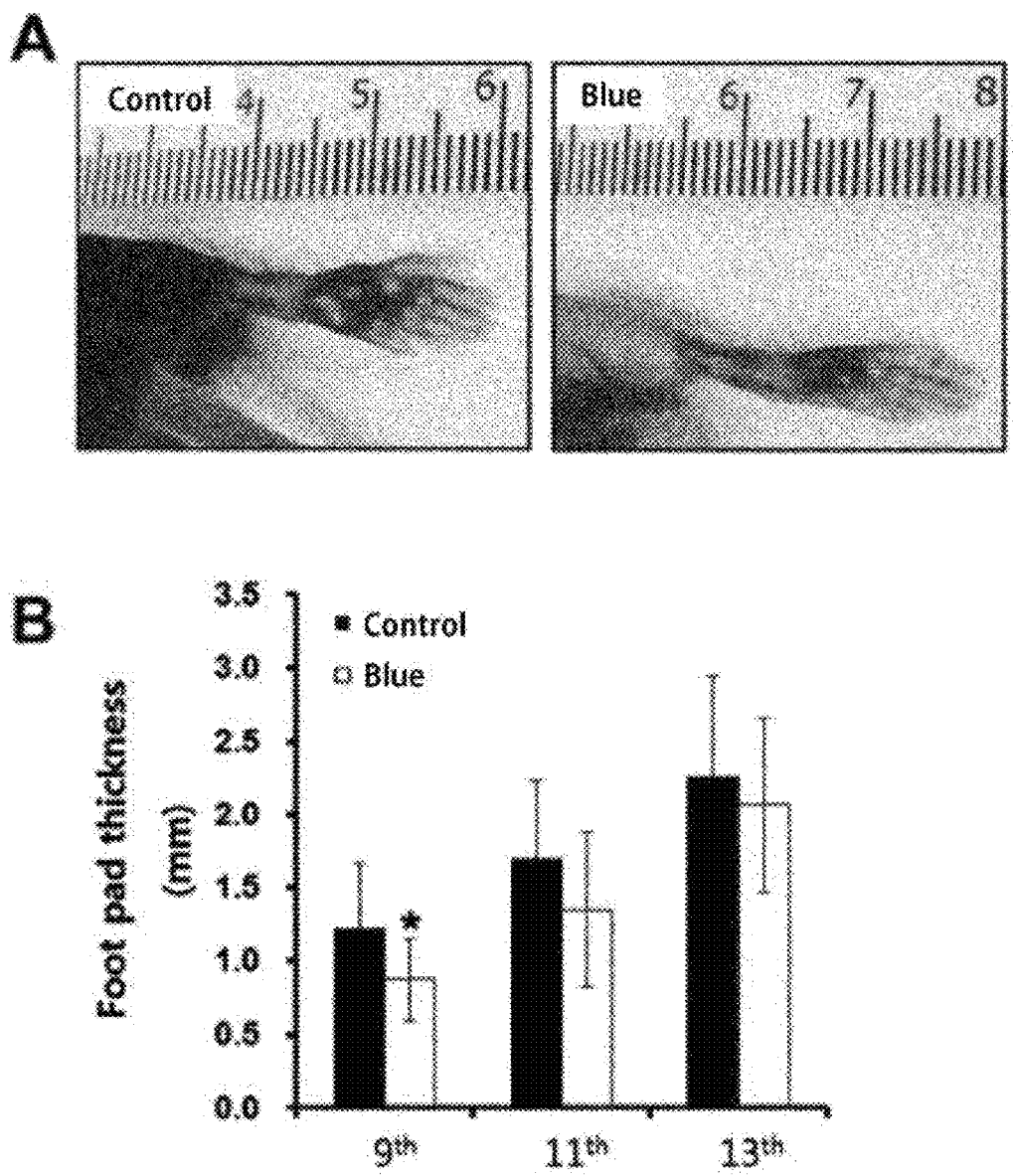
FIG. 8 is a result of measuring cell metastasis in Experimental Example 4.

As verified in FIG. 8, in an in-vivo effect of the LED blue treatment light, the proliferation rate of the tumor was measured by using the C57BL/6 mouse, and as a result, inhibition of the tumor growth in the early stage is shown, but there was no significant difference from the 9th repeating of the irradiation and pause of the LED blue treatment light.

As a result, it can be seen that the irradiation of the LED blue treatment light not only inhibits the cell growth rate of melanoma cells but also induces apoptosis using a mitochondria-dependent caspase pathway, and suppresses the growth of the melanoma in the early stage. Further, it is considered that the LED blue treatment light can be proved as a new therapeutic agent in the early stage of skin cancer.

Experimental Example 5. Measurement of Viabilities of Leukemic Cancer Cells and Lymphoma Cells The cells cultured in Preparation Examples 1-2 to 1-3 or the normal lymphocytes of Comparative Example 1 were divided by 2×10⁵/ml in a 4-well plate, irradiated with an LED of 450 nm at 15.6 mW/cm² for 2 hrs or 4 hrs, added with tetrazolium salts (WST) of ¹/₁₀ of the entire medium amount per well, and incubated at 37° C. for 3 hrs, and then cell viability was measured by measuring absorbance at 450 nm using an ELISA reader. The measurement results are illustrated in FIGS. 9A to 9C, in which FIG. 9A is a viability result of an A20 cell line, FIG. 9B is a viability result of an RAMOS cell line, and FIG. 9C is a viability result of normal human lymphocytes in Comparative Example 1.

Figure 9A:
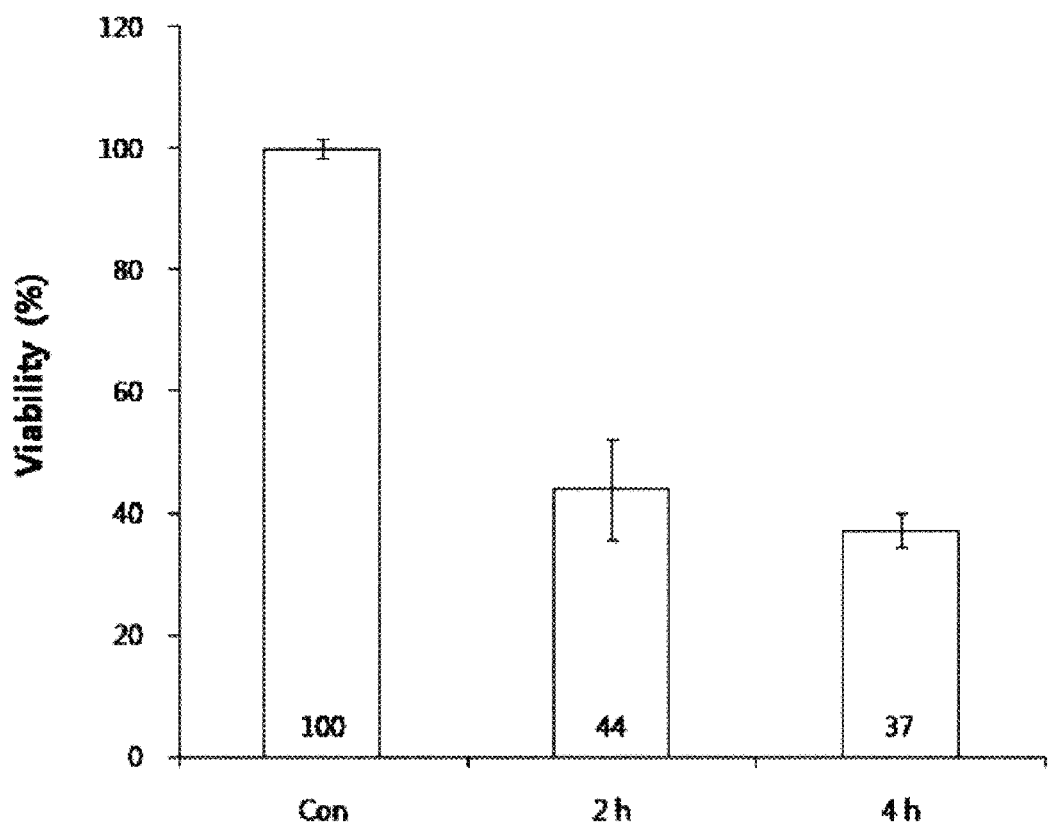
Figure 9B:
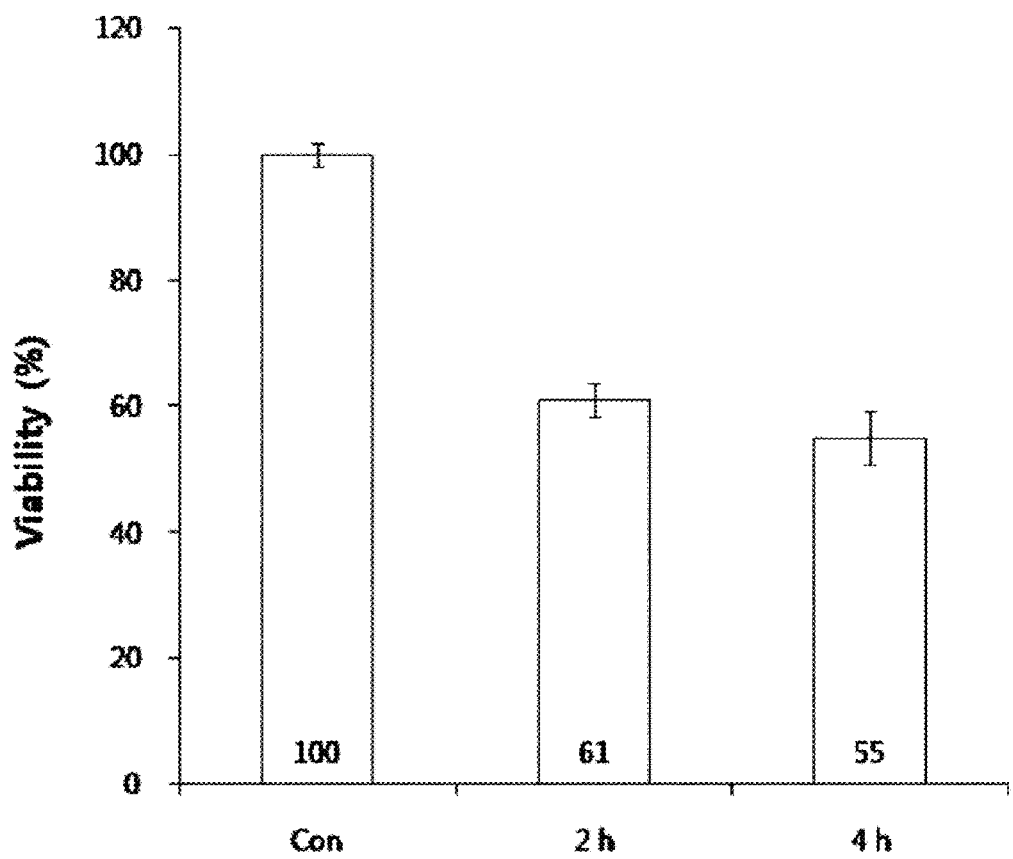

As verified in FIGS. 9A and 9B, in the A20 and RAMOS cell lines, it was verified that viability was significantly reduced from 2 hrs after irradiating the blue treatment light of the LED, and in the A20 cell line, the viabilities of 44% at 2 hrs and 37% at 4 hrs after irradiating the blue treatment light of the LED were shown. Further, in the RAMOS cell line, the viabilities of 61% at 2 hrs and 55% at 4 hrs after irradiating the blue treatment light of the LED were shown.

Figure 9C:
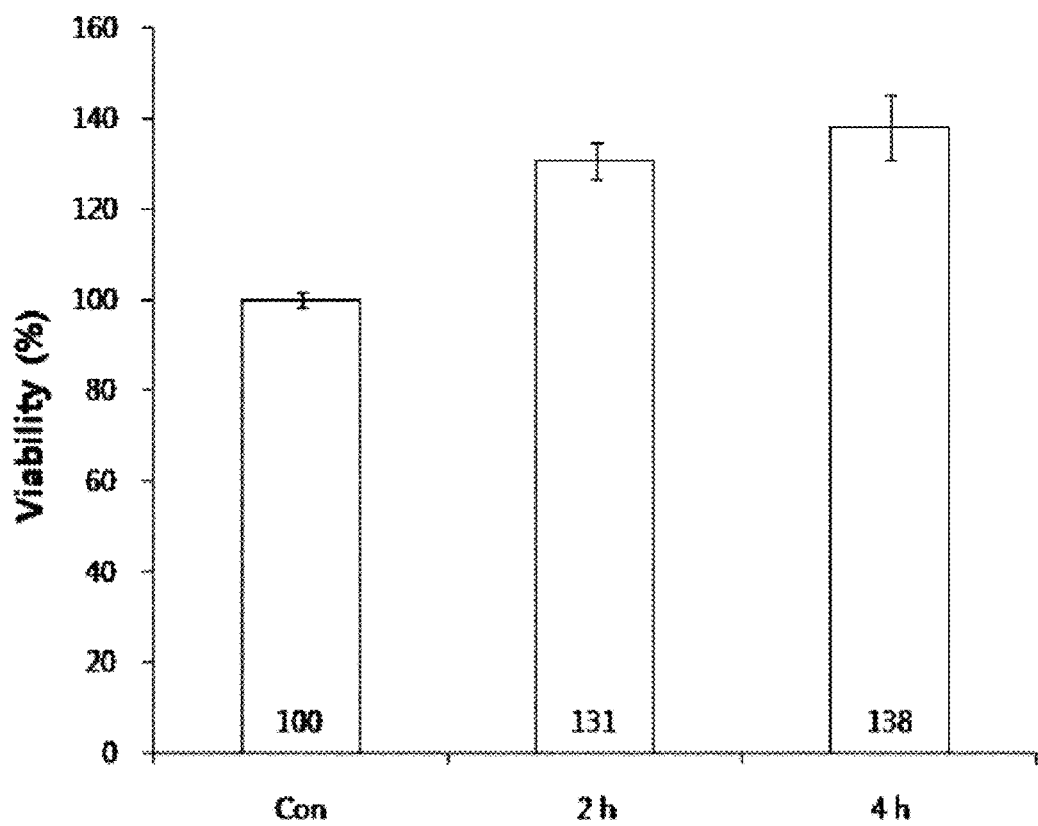

Meanwhile, as verified in FIG. 9C, unlike the A20 and RAMOS cell lines, it was verified that viability of the normal human lymphocytes was increased after irradiating the LED blue treatment light.

Experimental Example 6. Flow Cytometry Analysis of Leukemic Cancer Cells and Lymphoma Cells The cells incubated in Preparation Examples 1-2 and 1-3 were divided by 2×10⁵/ml in a dish of 6 cm, irradiated with LED blue treatment light of 450 nm for 2 hrs or 4 hrs at 15.6 mW/cm$^2$, and then washed twice with a phosphate buffered saline (PBS). Thereafter, the cells were analyzed by using a kit (Biolegend, 640914) of detecting apoptosis by staining the cells with Annexin V with FITC and propidium iodide (PI). The cells were stained by adding 2.5 μl of Annexin V and 5 μl of PI and flow cytometry was analyzed by using a flow cytometer (BD biosciences, FACSCalibur). The analysis result was illustrated in FIGS. 10A and 10B, and FIG. 10A is a flow cytometry result of the A20 cell line and FIG. 10B is a flow cytometry result of the RAMOS cell line.

Figure 10A:
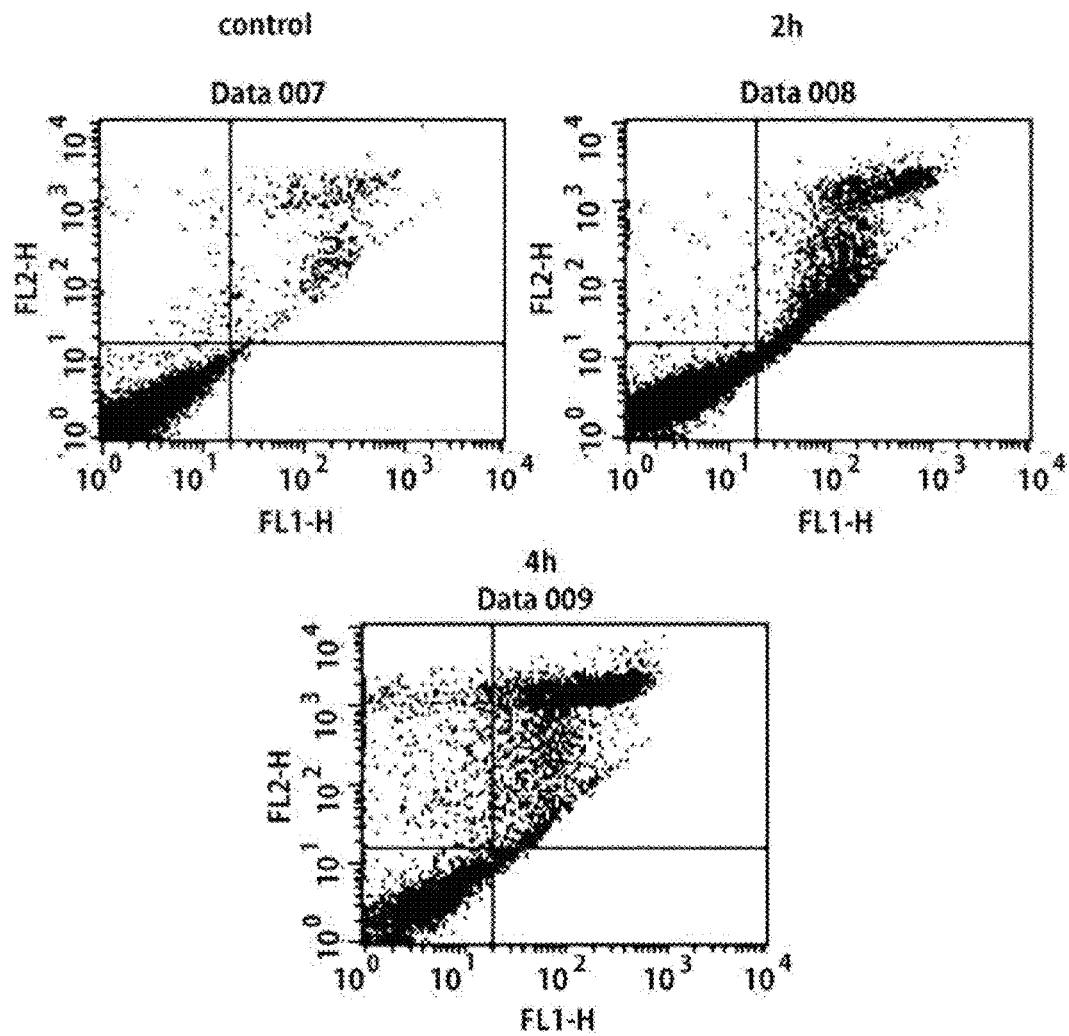

As verified in FIG. 10A, in the cell line irradiated by the LED blue treatment light for 2 hrs, 59% of survival and 36% of apoptosis and necrosis were shown, and in the cell line irradiated by the LED blue treatment light for 4 hrs, 40% of survival and 52% of apoptosis and necrosis were shown.

Figure 10B:
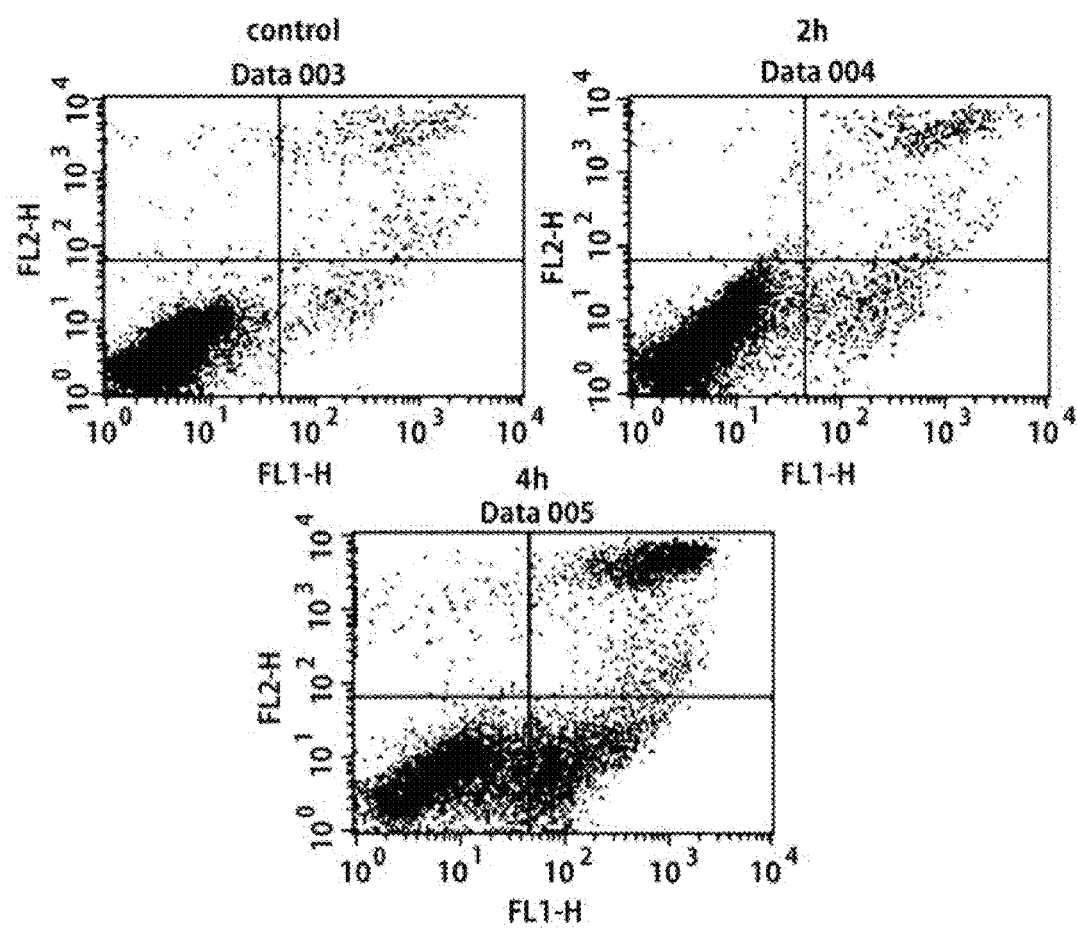

As verified in FIG. 10B, in the cell line irradiated by the LED blue treatment light for 2 hrs, 90% of survival was shown and had no large difference from a control group of 95% survival, and in the cell line irradiated by the LED blue treatment light for 4 hrs, 58% of survival, 21% of early apoptosis, and 19% of apoptosis and necrosis were shown.

Experimental Example 7. Measurement of Change in Mitochondria of A20 Cell After LED Irradiation The cells incubated in Preparation Examples 1-2 and 1-3 were divided by 2×10$^5$/ml in a dish of 6 cm, irradiated with LED blue treatment light of 450 nm for 2 hrs or 4 hrs at 15.6 mW/cm$^2$, and then washed twice with a phosphate buffered saline (PBS). Thereafter, the cells were stained by adding 10 μM of dihydroethidium and 0.1 μg/ml of rhodamine 123, respectively, and then membrane permeability of intracellular superoxide radical ($O_2^{\cdot-}$) and mitochondria was analyzed by using a flow cytometer and the analysis result is illustrated in FIG. 11.

Figure 11:
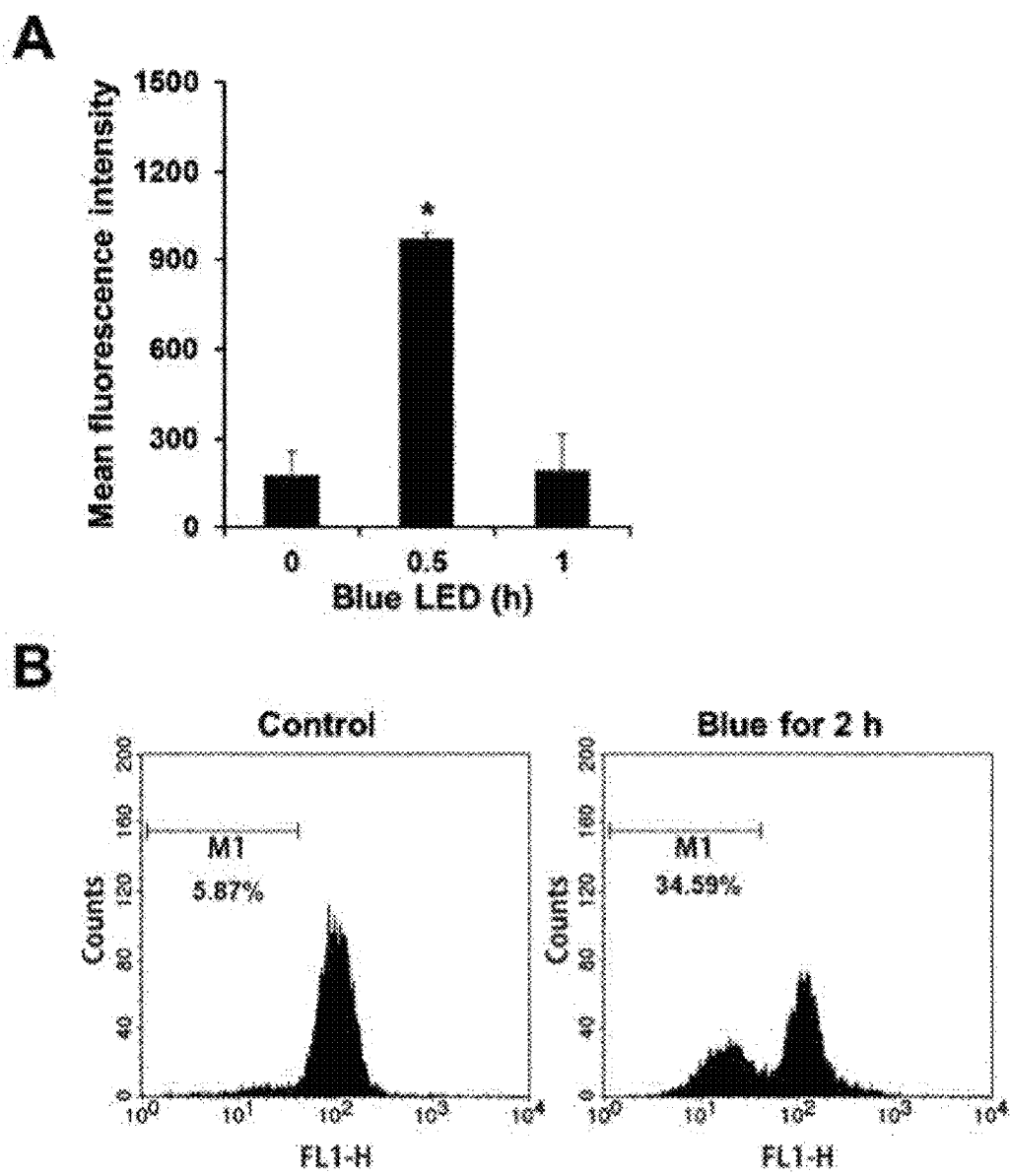
FIG. 11 is an analysis result of a leukemia animal experiment in Experimental Example 6.

As verified in FIG. 11, an increase in intracellular ROS and oxidative stress is characterized in the early apoptosis step in addition to the loss of the potential difference in the inner membrane of the mitochondria, and when the outer membrane of the mitochondria burst due to the decrease of the potential difference, pro-apoptotic proteins were released in the cytoplasm. It was verified that the level of the intracellular superoxide radical ($O_2^{\cdot-}$) after irradiating the blue treatment light was increased for 30 mins 5.4 times larger than the control group and then decreased for 1 hr, and permeability of the inner membrane of the mitochondria was increased up to 34.5% for 2 hrs.

Further, the A20 cells washed with the PBS was added with a cell destruction and protein extraction solution to extract the proteins from the cells and then the cell debris and the proteins were separated through centrifugation. The extracted proteins were moved to a membrane by electric force using a kit after electrophoresis and then reacted with antibodies of caspase-3, cleaved caspase-3, PARP, bcl-2, and bax, and reacted with secondary antibodies labeled with a luminescent material. Herein, the extracted proteins were reacted with an ECL reagent (Millipore, WBKLS0100) reacting with the luminescent material and thus the expression level of the proteins was measured by measuring the luminescence by using Fusion FX7 (Wilber lourmat). The measurement result is illustrated in FIG. 12.

Figure 12:
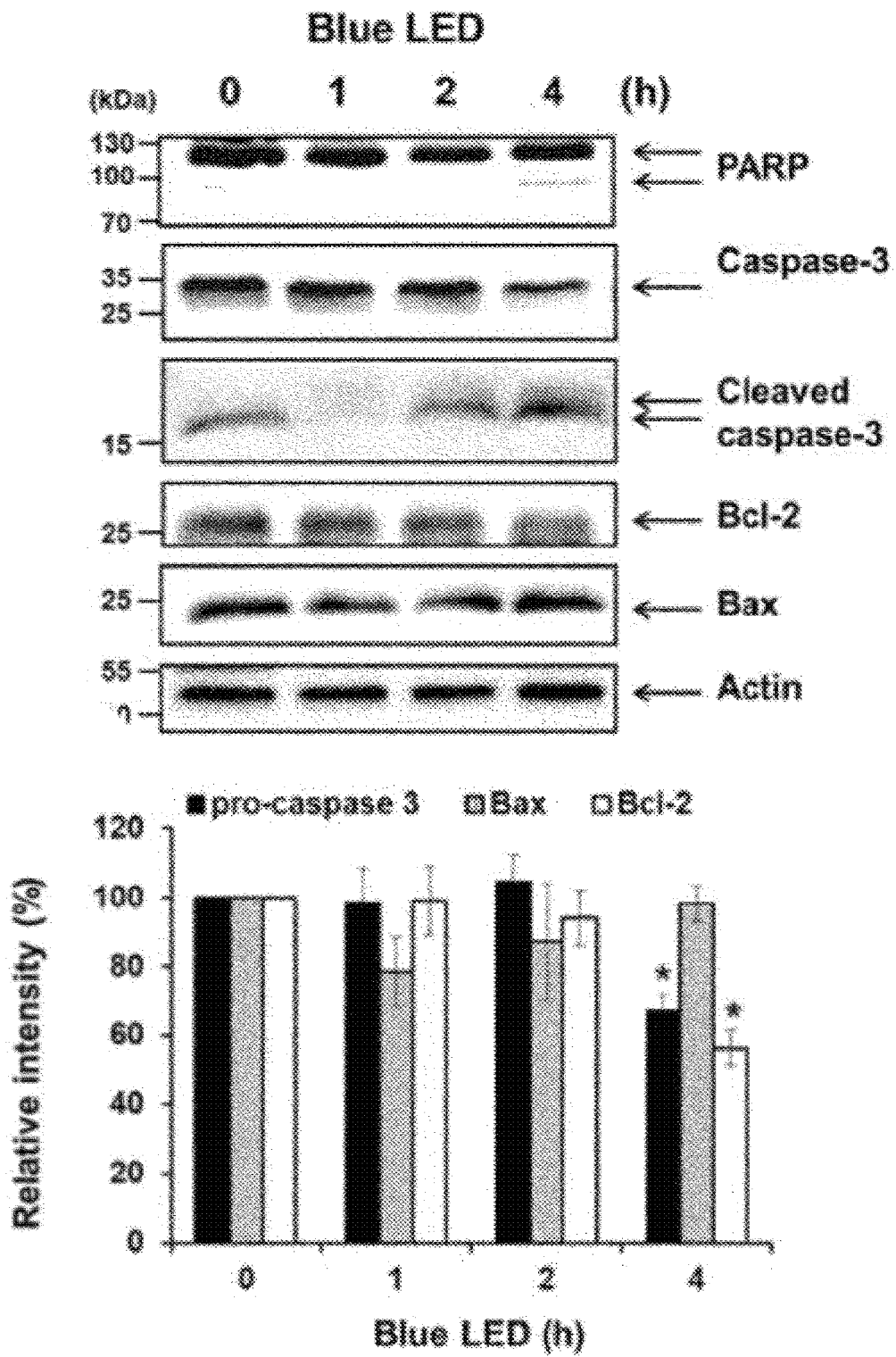
FIG. 12 is an analysis result of cell membrane permeability of an intracellular superoxide radical and mitochondria after irradiating blue treatment light in Experimental Example 7.

As verified in FIG. 12, it was verified that cleavage of the caspase-3 and the PARP was increased after irradiating the LED blue treatment light and the expression of bcl-2 was reduced, and the result is that it is determined that reduction of a membrane potential of mitochondria due to oxidative stress by increasing the intracellular ROS level after irradiation with the LED blue treatment light and apoptosis through an apoptotic pathway by caspase occur.

Experimental Example 8. Observation of Cell Organelle of A20 Cells after LED Irradiation The cells incubated in Preparation Examples 1-2 and 1-3 were divided by 2×10$^5$/ml in a dish of 6 cm, irradiated with LED blue treatment light of 450 nm for 4 hrs at 15.6 mW/cm$^2$, and then double-stained with 2% uranyl acetate and lead citrate through an immobilizing process and a dehydrating process, and then compared and observed under a transmission electron microscope (Zeiss EM10).

Figure 13:
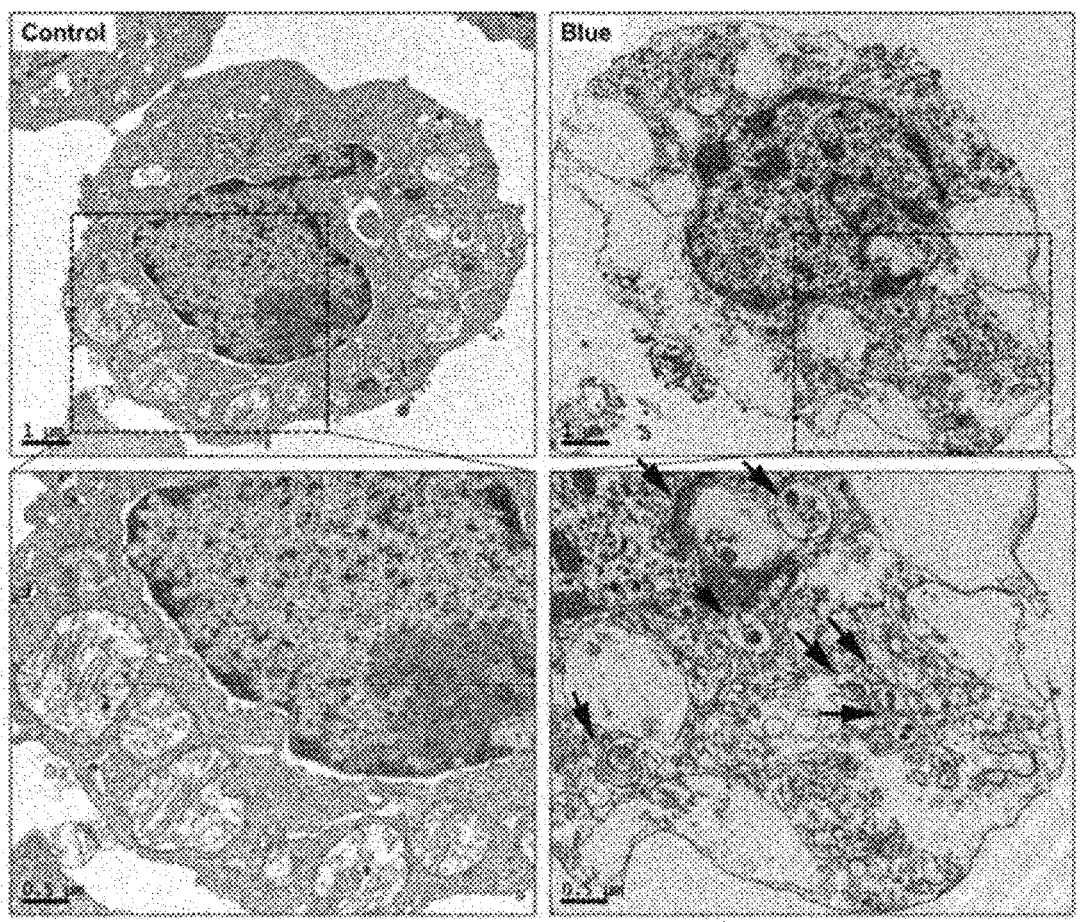
FIG. 13 is a photograph of formation of the endoplasmic reticulum in Experimental Example 8.

Since it was known that when autophagy as another type of programmed apoptosis occurred, these vesicles were found, in order to verify whether the vesicles shown by irradiation of the LED blue treatment light were autophagosome, the cells were stained. As a result, a lot of autophagic vacuoles in the cells were observed and it was observed that in the autophagic vacuoles, proteins having various sizes and intracellular organelles such as mitochondria were destroyed. Further, it was observed that when larger enlarged, the autophagic vacuoles covered by several layers of membrane, the autophagic vacuoles covered by a double membrane, and the vacuoles including the intracellular organelles were combined to form double membrane structural vesicles called autophagosome (FIG. 13).

Further, in order to verify that autophagy is caused by irradiation of the LED blue treatment light at a protein level, the expression level of the proteins related with the autophagy was observed through electrophoresis. As the protein with increased expression during autophagy, LC3 is included, and when autophagy occurs, LC3 of two types of LC3 is combined to the membrane of the autophagosome while converted to the LC3 type and thus becomes a direct index of the autophagosome.

Figure 14:
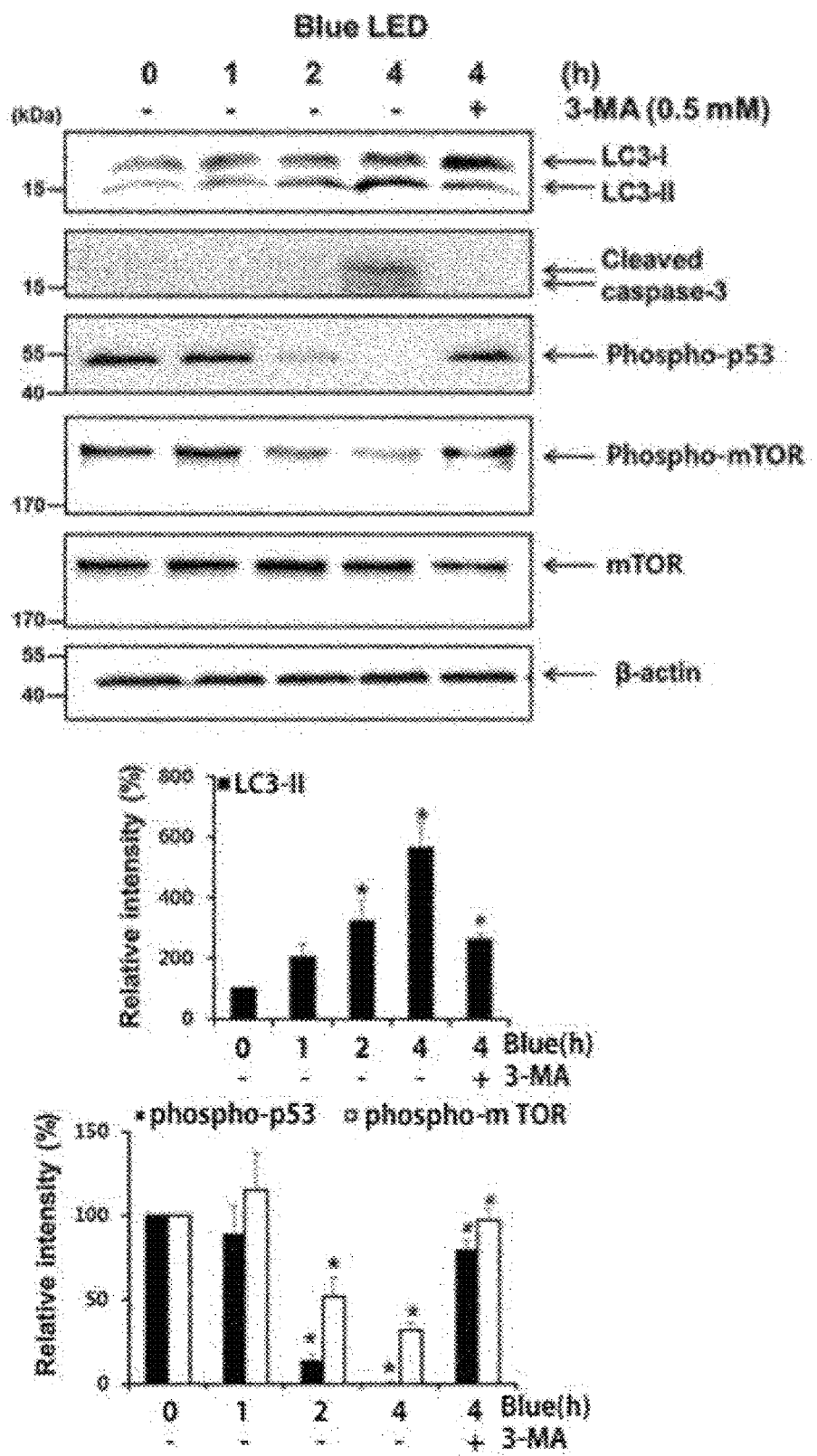
FIG. 14 is a result of measuring expression levels after irradiating blue treatment light in Experimental Example 8.

As verified in FIG. 14, expression of LC3 I and LC3 II types was increased after irradiation of the LED blue treatment light and expression of phosphorylated p53 and mTOR related with the autophagy was reduced. In order to examine a relationship between the autophagy caused by irradiation of the LED blue treatment light and the apoptosis, after 3-MA which was an autophagy inhibitor acting in early autophagy before the autophagosome is generated was pre-treated and expression of the LC3, the cleaved caspase-3, the phosphorylated p53 and the mTOR was verified. As a result, the expression of LC3 II and the cleaved caspase-3 was decreased and the expression of the phosphorylated p53 and the mTOR was increased. As a result, it was shown that the apoptosis by irradiating the LED blue treatment light was induced by stimulating an autophagy mechanism and can be associated with mitochondria damage and ROS generation.

Experimental Example 9. Leukemia Animal Experiment

A20 cells of 1×10$^6$ per mouse was injected by tail vein injection by using 6 to 7-week-old female Balb/c mice as a leukemia animal model. As a control group and an experimental group, 10 mice were set, respectively, and in the experimental group, the cells were immediately injected, irradiated with the LED blue treatment light of 450 nm at 15.6 mW/cm$^2$ for 3 hrs and then paused for 5 hrs without irradiation, and the irradiation and the pause were continuously repeated until all animals died. Further, until all of the animals died, the condition was observed twice daily. Further, statistical significance was analyzed by a Kaplan-Meier method and the analysis result is illustrated in FIG. 15.

As the observed result, from the 21-th day after cell injection, in some mice, symptoms of paraplegia or foot or tail injuries were observed, and particularly, the symptoms were shown in more mice in the control group than in the experimental group. Further, from the 28-th day after cell injection, in all mice, ascites symptoms were shown, and it was observed that it is difficult to breathe with less activity and eating amount from 2 to 3 days before death.

Figure 15:
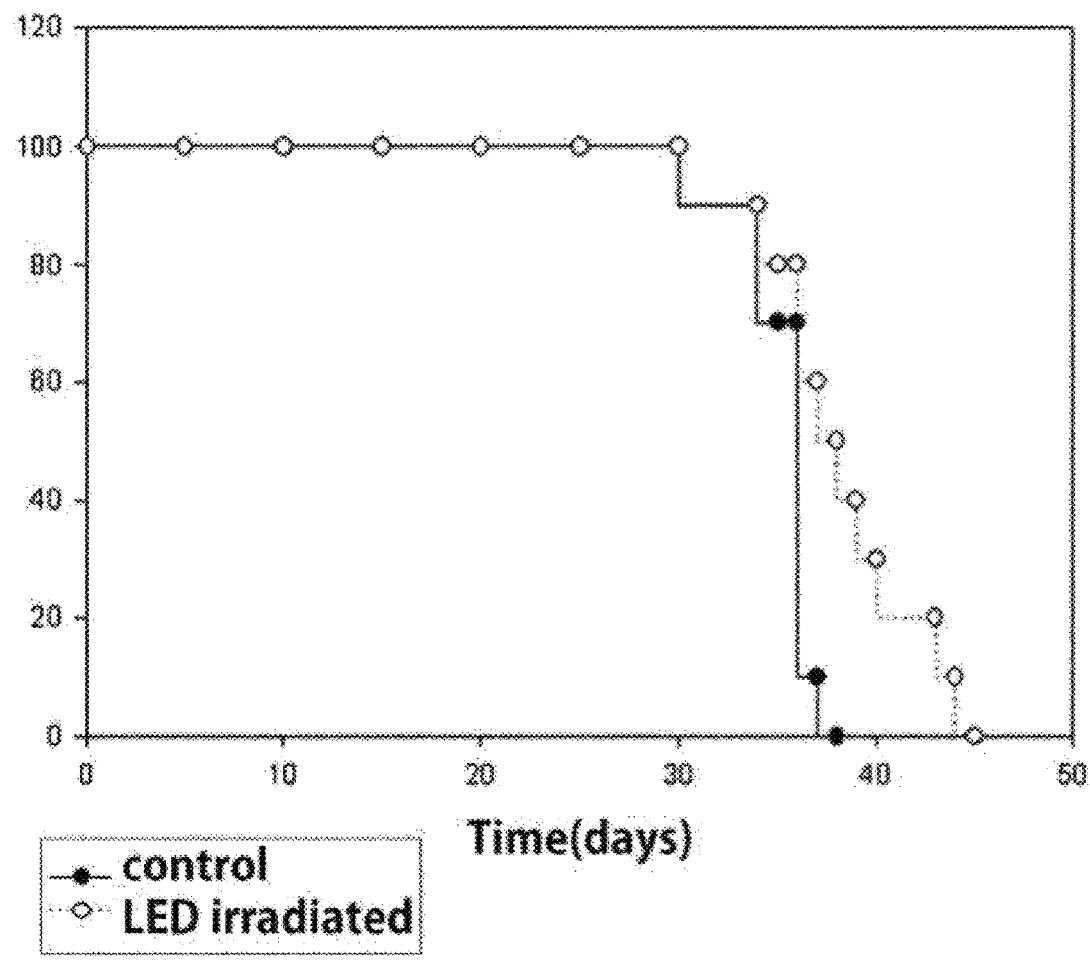
FIG. 15 is an experimental result of a leukemia animal experiment group after irradiating blue treatment light in Experimental Example 9 and a control group.

As verified in FIG. 15, a mean survival period was 36.6±0.34 days in the control group and 39.2±1.2 days in the experimental group irradiated with the LED blue treatment light, and it was verified that the result was statistically significant by the Kaplan-Meier method ($p<0.05$).

As a result, the irradiation of the LED blue treatment light not only inhibits the growth rate of the A20 cells but also promotes the autophagy through the production of intracellular ROS, suppression of phosphorylation of p53, and induces apoptosis using a mitochondria-dependent caspase pathway. In the leukemia animal model, the viability was increased compared to the control group and an anti-tumor effect was shown from after the experiment was finished, and it is considered that the LED blue treatment light can be proven as a new therapeutic agent in blood cancer.

Experimental Example 10. Experiment for Measuring Invasion of Human Fibrosarcoma Cells In invasion and metastasis of the cancer, in order to verify an effect of irradiating the LED blue treatment light by ability that the cancer cells penetrated through a reconstituted basement membrane, the human fibrosarcoma cells migrated beyond a matrigel-coated filter were analyzed by using a transwell cell culture chamber (SPL Life Sciences, Korea).

The cells incubated in Preparation Examples 1-2 and 1-3 were divided by $3 \times 10^4$/well in an upper chamber coated with matrigel, put with a serum-free medium in a lower chamber, irradiated with the blue treatment light of the LED of 450 nm at 15.6 mW/cm$^2$ for 10 mins and then incubated at 37° C. for 6 hrs. The cells invaded by moving from the upper chamber to the lower chamber through the matrigel-coated transwell filter were stained with crystal violet and then observed by an optical microscope, and the result is illustrated in FIG. 16.

Figure 16:
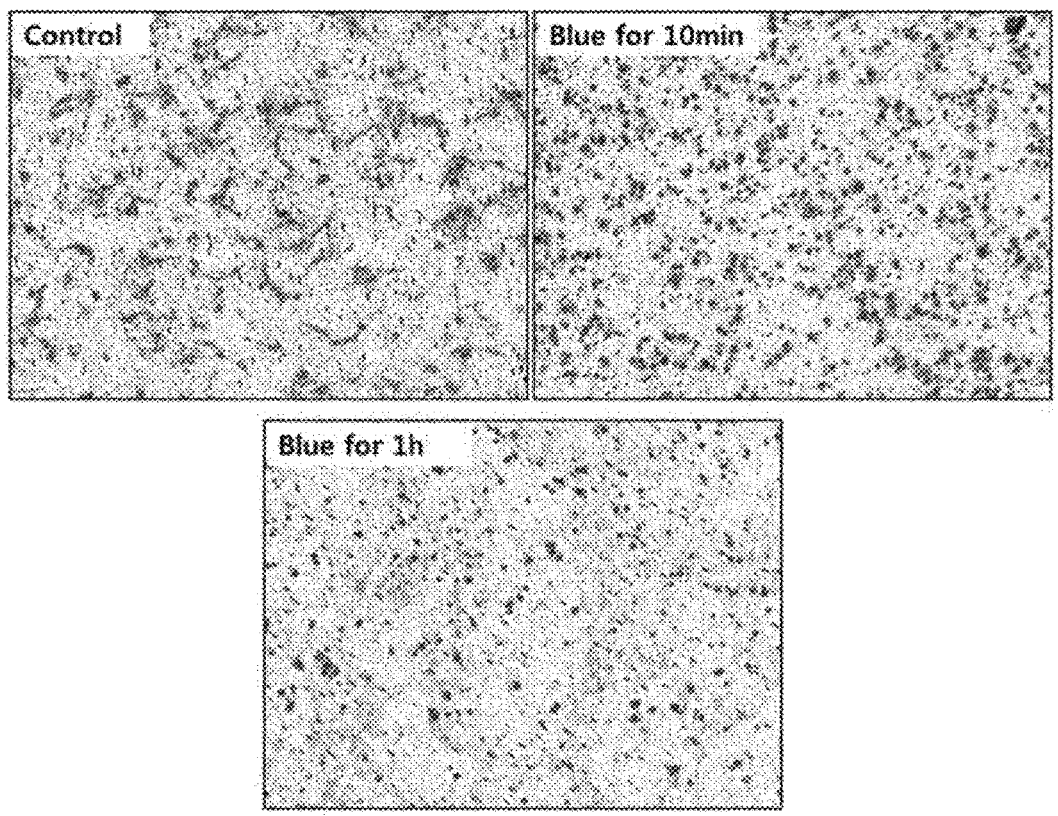
FIG. 16 is a result of observing sarcoma cells after irradiating blue treatment light in Experimental Example 10.

As verified in FIG. 16, the human fibrosarcoma cells invaded by moving to the lower chamber were reduced dependently at an irradiation time of the LED blue treatment light.

Experimental Example 11. Measurement of Intracellular ROS of HT-1080 Cells After LED Irradiation The cells incubated in Preparation Examples 1-2 and 1-3 were divided by $1 \times 10^5$/ml in a dish of 6 cm, irradiated with LED blue treatment light of 450 nm at 15.6 mW/cm$^2$ for 10 mins, incubated at 37° C. for 5 hrs, and then washed twice with a phosphate buffered saline (PBS). Thereafter, the cells were stained by adding 10 μM of dihydroethidium and then an intracellular superoxide radical ($O_2^{\cdot-}$) level was analyzed by using a flow cytometer and the analyzed result is illustrated in FIG. 17.

Figure 17:
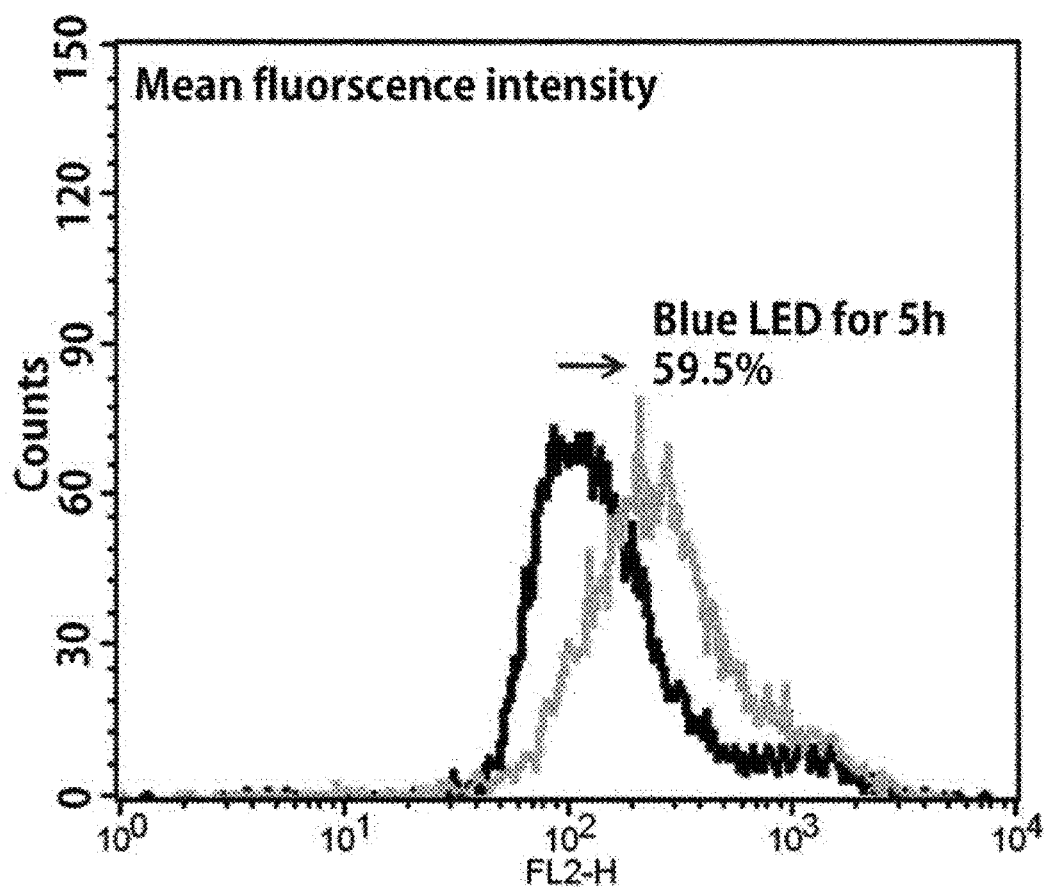
FIG. 17 is an analysis result of superoxide after irradiating blue treatment light in Experimental Example 11.
Figure 18A:
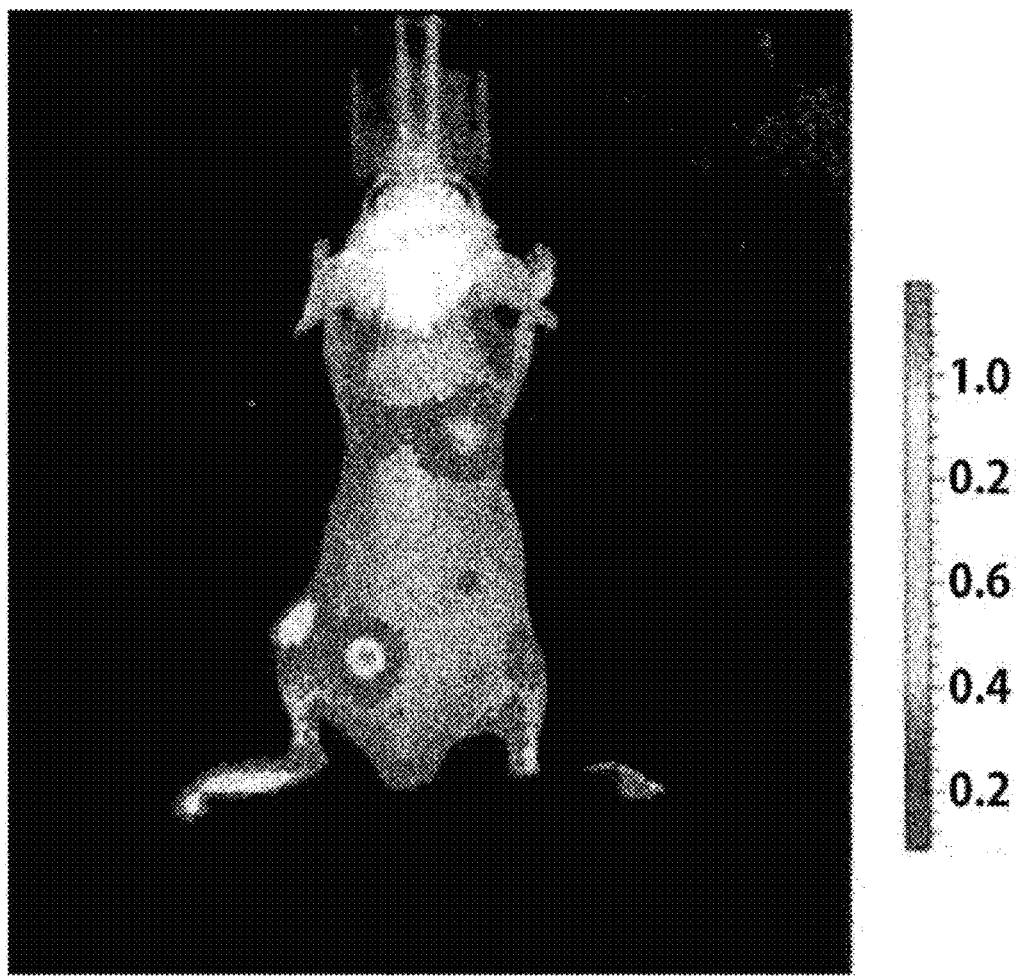
Figure 18B:
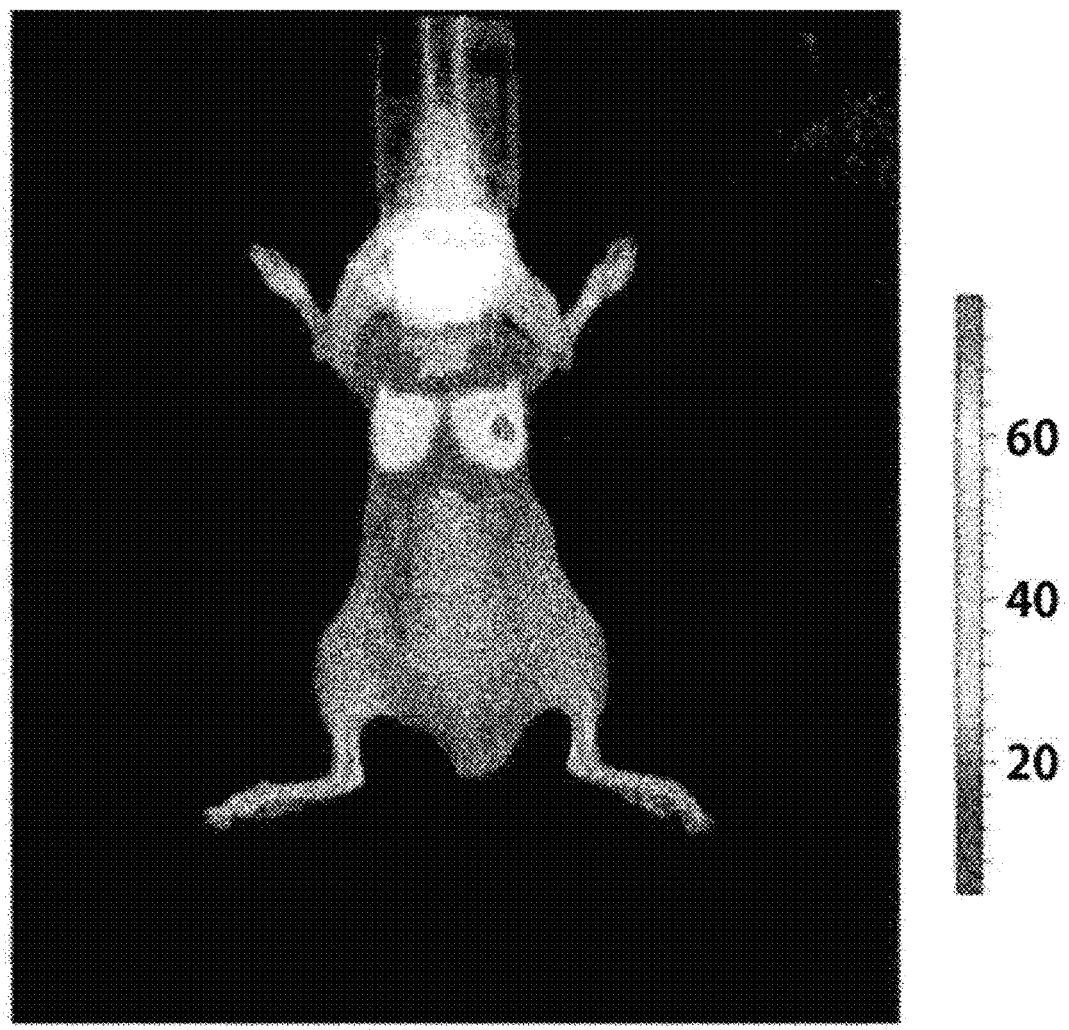

As verified in FIG. 17, it was verified that the intracellular superoxide radical ($O_2^{\cdot-}$) level after irradiation of the blue treatment light was increased by 59.5% compared to the control group for 5 hrs.

As a result, it was shown that the irradiation of the LED blue treatment light had effects of promoting generation of the intracellular ROS in the HT-1080 cells and reducing the invasion of the cells and thus had a possibility as a new cancer treatment agent.

Meanwhile, an experiment was performed by using a CT26-luc cell line through genetic manipulation to obtain an optical image by luciferin by injecting a luc gene to CT26 mouse rectal cancer cells.

The CT26-luc cell line was injected by $5 \times 10^4$ through the tail vein and optical images were obtained from the fifth day and metastasis and the like were observed.

Like FIGS. 8A and 8B, it was verified that in the non-irradiated group compared with the group irradiated with the blue light, metastasis to other organs and tissues except for the lung often occurred. It can be interpreted that it is verified that metastatic cancer cells deviated from the lungs are inhibited from being developed into metastatic cancer by blue light.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A cancer cell growth inhibition and killing device using a blue light LED,
the device comprising:
a bed part which has a top plate configured to support a body of a patient, wherein the bed part includes a vertical table having a predetermined length of which an upper end is rotatably supported through a hinge pin on the lower surface of the top plate and front and rear cylinder members of which load front ends are connected to front and rear lower surfaces of the top plate through the pin member and are vertically operated to obliquely shift a horizontal state of the top plate based on the hinge pin, respectively;
a main body part provided with a treatment space, which has a predetermined size and on which the bed part is disposed, and having a chamber which is divided by the treatment space and a transparent plate formed of a light-transmitting material to thus form a treatment light generation space; and
a treatment light generation unit which is configured to generate a blue treatment light consisting of a wavelength band of 450 nm to 470 nm when power is applied so that the blue treatment light can penetrate the subcutaneous tissue of the body and thereby stimulate and kill cancer cells moving along blood vessels, and which is provided in the chamber so as to irradiate the treatment space with the blue treatment light after the blue treatment light has penetrated though the transparent plate,
wherein the patient's body is supported by the bed part, the patient having previously been diagnosed as having cancer, and
wherein the blue treatment light is capable of (1) increasing expression of cleaved caspase-3 cleaved in cancel cells of the patient and (2) increasing production of reactive oxygen species (ROS) and phosphorylation of p53 in cancer cells of the patient.
2. The cancer cell growth inhibition and killing device of claim 1, wherein the treatment light generation unit includes LEDs that generate the blue treatment light consisting of a wavelength band of 450 to 470 nm when the power is applied, lenses that guide light so that the blue treatment light generated in the LED is convergence-irradiated to the body, and heat dissipation members that discharge heat generated when the light of the LED is emitted to the outside so that a central wavelength of the blue treatment light is not changed.

3. The cancer cell growth inhibition and killing device of claim 1, wherein the main body part includes at least one ventilation fan at the outside of the chamber corresponding to the treatment light generation space to ventilate indoor air in the treatment light generation space to the outside.

4. The cancer cell growth inhibition and killing device of claim 1, wherein the main body part includes a reflective sheet that reflects the treatment light to the inner surface to enhance a light irradiation rate for the living body.

5. The cancer cell growth inhibition and killing device of claim 1, wherein the main body part includes an upper main body part having the upper treatment light generation space based on the bed part, a lower main body part having the lower treatment light generation space, and a hinge member pivoting the upper main body part with respect to the lower main body part to open and close the treatment space.

6. The cancer cell growth inhibition and killing device of claim 1, wherein the vertical table includes an internal pipe having a predetermined length of which an upper end is connected to the top plate through the hinge pin and an external pipe having a predetermined length to which a lower end of the internal pipe is inserted to be vertically guided.

* * * * *